(12) United States Patent
Follmann et al.

(10) Patent No.: US 8,765,769 B2
(45) Date of Patent: Jul. 1, 2014

(54) RING-FUSED 4-AMINOPYRIMIDINES AND USE THEREOF AS STIMULATORS OF SOLUABLE GUANYLATE CYCLASES

(75) Inventors: Markus Follmann, Köln (DE); Johannes-Peter Stasch, Solingen (DE); Gorden Redlich, Bochum (DE); Jens Ackerstaff, Berlin (DE); Nils Griebenow, Dormagen (DE); Andreas Knorr, Erkrath (DE); Frank Wunder, Wuppertal (DE); Volkhart Min-Jian Li, Velbert (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/704,980

(22) PCT Filed: Jul. 5, 2011

(86) PCT No.: PCT/EP2011/061306
§ 371 (c)(1),
(2), (4) Date: Feb. 28, 2013

(87) PCT Pub. No.: WO2012/004259
PCT Pub. Date: Jan. 12, 2012

(65) Prior Publication Data
US 2013/0172372 A1 Jul. 4, 2013

(30) Foreign Application Priority Data

Jul. 9, 2010 (DE) .......................... 10 2010 031 148
Apr. 21, 2011 (DE) .......................... 10 2011 007 891

(51) Int. Cl.
| | | |
|---|---|---|
| A01N 43/54 | (2006.01) | |
| A01N 43/90 | (2006.01) | |
| A61K 31/517 | (2006.01) | |
| A61K 31/519 | (2006.01) | |

(52) U.S. Cl.
USPC .................... 514/258.1; 514/265.1; 544/279; 544/280

(58) Field of Classification Search
USPC ..................... 544/279, 280; 514/258.1, 265.1
See application file for complete search history.

(56) References Cited

U.S. PATENT DOCUMENTS

| | | | |
|---|---|---|---|
| 5,976,523 | A | 11/1999 | Awaya et al. |
| 6,180,656 | B1 | 1/2001 | Furstner et al. |
| 6,451,805 | B1 | 9/2002 | Straub et al. |
| 6,743,798 | B1 | 6/2004 | Straub et al. |
| 6,833,364 | B1 | 12/2004 | Straub et al. |
| 6,903,089 | B1 | 6/2005 | Stasch et al. |
| 7,173,037 | B2 | 2/2007 | Alonso-Alija et al. |
| 7,410,973 | B2 | 8/2008 | Fuerer et al. |
| 7,414,136 | B2 | 8/2008 | Matsumura et al. |
| 7,541,367 | B2 | 6/2009 | Chiu et al. |
| 8,242,272 | B2 | 8/2012 | Jimenez et al. |
| 8,309,551 | B2 | 11/2012 | Schirok et al. |
| 2004/0235863 | A1 | 11/2004 | Feurer et al. |
| 2011/0218202 | A1 | 9/2011 | Brockunier et al. |
| 2011/0224197 | A1 | 9/2011 | Henkel et al. |
| 2013/0072492 | A1 | 3/2013 | Raghavan et al. |
| 2013/0172372 | A1 | 7/2013 | Follmann et al. |
| 2013/0178475 | A1 | 7/2013 | Moore et al. |

FOREIGN PATENT DOCUMENTS

| | | |
|---|---|---|
| CA | 2804470 | 1/2012 |
| CA | 2809911 | 3/2012 |
| CA | 2833698 | 10/2012 |
| CA | 2834901 | 11/2012 |
| CN | 1613849 | 5/2005 |
| EP | 0634413 | 1/1995 |
| WO | 0183490 | 11/2001 |
| WO | WO 2009145814 A2 * | 12/2009 |

OTHER PUBLICATIONS

Becker et al., "NO-Independent Regulatory Site of Direct sGC Stimulators like YC-1 and BAY 41-2272," BMC Pharmacology, 2001, 1: 13.
Cheng et al., "Potential Purine Antagonists VII. Synthesis of 6-Alkylpyrazolo-[3,4-d]pyrimidines," J. Org. Chem., 1958, 23:191-200.
Evgenov et al., "NO-independent stimulators and activators of soluble guanylate cyclase: discovery and therapeutic potential," Nat. Rev. Drug. Disc, Sep. 2006, 5:543-547.
Goldberg et al., "Stimulation of Human Platelet Guanylate Cyclase by Fatty Acids," J. Biol. Chem., 1977, 252, 1279-1285.
Hassan et al., "Aryl-Aryl Bond Formation One Century after the Discovery of the Ullmann Reaction," Chem. Rev. 2002, 102: 1359-1469.
Ko et al., "YC-1, a Novel Activator of Platelet Guanylate Cyclase," Blood, Dec. 1994, 84(12): 4226-4233.
Mittendorf et al., "Discovery of Riociguat (BAY 63-2521): A Potent, Oral Stimulator of Soluble Guanylate Cyclase for the Treatment of Pulmonary Hypertension," Chem. Med. Chem., 2009, 4: 853-865.
Malsch et al., "Effect of YC-1, an NO-independent, superoxide-sensitive stimulator of soluble guanylyl cyclase, on smooth muscle responsiveness to nitrovasodilators," Brit. J. Pharm., 1997, 120: 681-689.
Pettibone et al., "A Structurally Novel Stimulator of Guanylate Cyclase with Long-Lasting Hypotensive Activity in the Dog," Euro. J. of Pharmacology, 1985, 116: 307-312.

(Continued)

Primary Examiner — Deepak Rao
Assistant Examiner — Alexander R Pagano
(74) Attorney, Agent, or Firm — Karen B. King

(57) ABSTRACT

The present application relates to novel fused 4-aminopyrimidines, to processes for preparation thereof, to the use thereof, alone or in combinations, for treatment and/or prophylaxis of diseases and to the use thereof for production of medicaments for the treatment and/or prophylaxis of diseases, especially for treatment and/or prophylaxis of cardiovascular disorders.

6 Claims, No Drawings

(56) References Cited

OTHER PUBLICATIONS

Sharkovska et al., "Nitric oxide-independent stimulation of soluble guanylate cyclase reduces organ damage in experimental low-renin and high-renin models," J. Hypertnesion, 2010, 28(8):1666-1675.
Stasch et al., "Soluble Guanylate Cyclase as an Emerging Therapeutic Target in Cardiopulmonary Disease," Circulation, May 2011, 123: 2263-2273.
Winn et al., "2-(Alkylamino)nicotinic Acid and Analogs. Potent Angiotensin II Antagonists," J. Med. Chem 1993, 36: 2676-2688.
Witte et al., "Experimental heart failure in rats: effects on cardiovascular circadian rhythms and on myocardial β-adrenergic signaling," Cardiovascular Research, 2000, 47: 350-358.
Wu et al., "YC-1 inhibited human platelet aggregation through NO-independent activation of soluble guanylate cyclase," Br J. Pharmacol. Oct. 1995, 116(3):1973-1978.
Wunder et al., "A cell-based cGMP assay useful for ultra-high-throughput screening and identification of modulators of the nitric oxide/cGMP pathway," Anal. Biochem., 2005, 339:104-112.
Yu et al., "Vasorelaxant Effect of Isoliquiritigenin, A novel soluble guanylate cyclase activator, in rat aorta," Brit. J. of Pharmacology, 1995, 114: 1587-1594.
U.S. Appl. No. 13/806,425.
U.S. Appl. No. 13/736,692.
U.S. Appl. No. 13/599,975.
U.S. Appl. No. 14/115,870.

\* cited by examiner

RING-FUSED 4-AMINOPYRIMIDINES AND USE THEREOF AS STIMULATORS OF SOLUABLE GUANYLATE CYCLASES

The present application relates to novel fused 4-aminopyrimidines, to processes for preparation thereof, to the use thereof, alone or in combinations, for treatment and/or prophylaxis of diseases and to the use thereof for production of medicaments for the treatment and/or prophylaxis of diseases, especially for treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family known to date can be divided into two groups either according to structural features or according to the type of ligands: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. This is of central importance for the activation mechanism. NO can bind to the iron atom of heme and thus markedly increase the activity of the enzyme. Heme-free preparations cannot, by contrast, be stimulated by NO. Carbon monoxide (CO) is also able to bind to the central iron atom of heme, but the stimulation by CO is much less than that by NO.

Through the formation of cGMP and the resulting regulation of phosphodiesterases, ion channels and protein kinases, guanylate cyclase plays a crucial role in different physiological processes, more particularly in the relaxation and proliferation of smooth muscle cells, in platelet aggregation and platelet adhesion, and in neuronal signal transmission, and also in the event of disorders based on disruption of the abovementioned processes. Under pathophysiological conditions, the NO/cGMP system can be suppressed, which can lead, for example, to hypertension, platelet activation, increased cell proliferation, endothelial dysfunction, atherosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Therapeutic stimulation of soluble guanylate cyclase has to date been accomplished using exclusively compounds such as organic nitrates, the effect of which is based on NO. The latter is formed by bioconversion and activates soluble guanylate cyclase by attack at the central iron atom of heme. In addition to the side effects, the development of tolerance is one of the crucial disadvantages of this mode of treatment.

In the last few years, there have been descriptions of some compounds which stimulate soluble guanylate cyclase directly, i.e. without prior release of NO, for example 3-(5'-hydroxymethyl-2'-furyl)-1-benzylindazole [YC-1; Wu et al., *Blood* 84 (1994), 4226; Mülsch et al., *Brit. J. Pharmacol.* 120 (1997), 681], fatty acids [Goldberg et al., *J. Biol. Chem.* 252 (1977), 1279], diphenyliodonium hexafluorophosphate [Pettibone et al., *Eur. J. Pharmacol.* 116 (1985), 307], isoliquiritigenin [Yu et al., *Brit. J. Pharmacol.* 114 (1995), 1587] and various substituted pyrazole derivatives (WO 98/16223).

As stimulators of soluble guanylate cyclase, WO 00/06569 discloses fused pyrazole derivatives, and WO 03/095451 carbamate-substituted 3-pyrimidinylpyrazolopyridines. WO 2010/065275 discloses substituted pyrrolo- and dihydropyridopyrimidines as sGC activators.

It was an object of the present invention to provide novel substances which act as very potent stimulators of soluble guanylate cyclase.

The present invention provides compounds of the general formula (I)

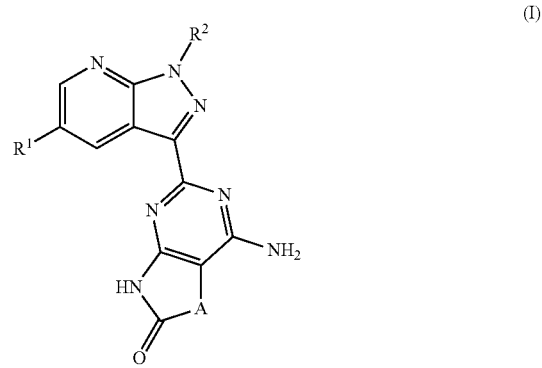

in which
A is $(C_1-C_3)$-alkanediyl or a group of the formula

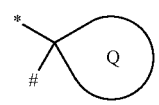

where
\* is the attachment site to the pyrimidine ring,
\# is the attachment site to the carbonyl group,
the ring Q is a 4- to 6-membered heterocycle,
and
where $(C_1-C_3)$-alkanediyl may be substituted by 1 or 2 substituents independently selected from the group of fluorine, trifluoromethyl, $(C_1-C_4)$-alkyl, hydroxyl and amino,
in which $(C_1-C_4)$-alkyl may be substituted by 1 to 3 substituents independently selected from the group of fluorine, trifluoromethyl and hydroxyl,
$R^1$ is hydrogen or fluorine,
$R^2$ is $(C_1-C_6)$-alkyl or benzyl,
where $(C_1-C_6)$-alkyl is substituted by one trifluoromethyl substituent,
where $(C_1-C_6)$-alkyl may be substituted by 1 to 3 fluorine substituents,
and
where benzyl is substituted by 1 to 3 fluorine substituents,
and the N-oxides, salts, solvates, salts of N-oxides and solvates of the N-oxides or salts thereof.

Inventive compounds are the compounds of the formula (I) and the salts, solvates and solvates of the salts thereof, the compounds, encompassed by formula (I), of the formulae specified hereinafter and the salts, solvates and solvates of the salts thereof, and the compounds encompassed by formula (I) and specified hereinafter as working examples and the salts, solvates and solvates of the salts thereof, to the extent that the compounds encompassed by formula (I) and specified hereinafter are not already salts, solvates and solvates of the salts.

Inventive compounds are likewise N-oxides of the compounds of the formula (I) and the salts, solvates and solvates of the salts thereof.

Preferred salts in the context of the present invention are physiologically acceptable salts of the inventive compounds. Also encompassed are salts which are not themselves suitable for pharmaceutical applications but can be used, for example, for isolation or purification of the inventive compounds.

Physiologically acceptable salts of the inventive compounds include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the inventive compounds which, in the solid or liquid state, form a complex by coordination with solvent molecules. Hydrates are a specific form of the solvates in which the coordination is with water. Solvates preferred in the context of the present invention are hydrates.

The inventive compounds may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. It is possible to isolate the stereoisomerically homogeneous constituents from such mixtures of enantiomers and/or diastereomers in a known manner; preference is given to using chromatographic methods for this purpose, especially HPLC chromatography on an achiral or chiral phase.

Where the inventive compounds can occur in tautomeric forms, the present invention encompasses all the tautomeric forms.

The present invention also encompasses all suitable isotopic variants of the inventive compounds. An isotopic variant of an inventive compound is understood here to mean a compound in which at least one atom within the inventive compound has been exchanged for another atom of the same atomic number, but with a different atomic mass than that which occurs usually or predominantly in nature. Examples of isotopes which can be incorporated into an inventive compound are those of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of an inventive compound, such as, more particularly, those in which one or more radioactive isotopes have been incorporated, may be of benefit, for example, for the study of the mechanism of action or of the active ingredient distribution in the body; due to the comparative ease of preparability and detectability, compounds labeled particularly with $^3$H or $^{14}$C isotopes are suitable for this purpose. Furthermore, the incorporation of isotopes, for example of deuterium, can lead to particular therapeutic advantages as a consequence of greater metabolic stability of the compound, for example an extension of the half-life in the body or a reduction in the active dose required; such modifications of the inventive compounds may therefore, in some cases, also constitute a preferred embodiment of the present invention. Isotopic variants of the inventive compounds can be prepared by the processes known to those skilled in the art, for example by the methods described below and the procedures described in the working examples, by using corresponding isotopic modifications of the respective reagents and/or starting compounds.

The present invention also encompasses prodrugs of the inventive compounds. The term "prodrugs" includes compounds which may themselves be biologically active or inactive but are converted to inventive compounds while resident in the body (for example metabolically or hydrolytically).

In the formula of the group which may represent A, the end point of the line marked by the symbol * or # does not represent a carbon atom or a CH$_2$ group, but is part of the bond to the respective atom to which A is attached.

In the context of the present invention, unless specified otherwise, the substituents are defined as follows:

Alkyl in the context of the invention is a linear or branched alkyl radical having 1 to 4 carbon atoms. Preferred examples include: methyl, ethyl, n-propyl, isopropyl, n-butyl, isobutyl, 1-methylpropyl, tert-butyl.

Alkanediyl in the context of the invention is a linear divalent alkyl radical having 1 to 3 carbon atoms. Examples include: methylene, ethane-1,2-diyl or propane-1,3-diyl.

Heterocycle in the context of the invention is a saturated heterocycle having a total of 4 to 6 ring atoms, which contains one or two ring heteroatoms from the group of N, O and/or S and is joined via a ring carbon atom. Examples include: azetidinyl, oxetanyl, pyrrolidinyl, pyrazolidinyl, tetrahydrofuranyl, piperidinyl, piperazinyl, tetrahydropyranyl, morpholinyl and thiomorpholinyl. Preference is given to azetidinyl, oxetanyl, pyrrolidinyl, tetrahydrofuranyl, piperidinyl and tetrahydropyranyl.

If radicals in the inventive compounds are substituted, the radicals may be mono- or polysubstituted, unless specified otherwise. In the context of the present invention, all radicals which occur more than once are defined independently of one another. Substitution by one, two or three identical or different substituents is preferred.

Preference is given in the context of the present invention to compounds of the general formula (I-1)

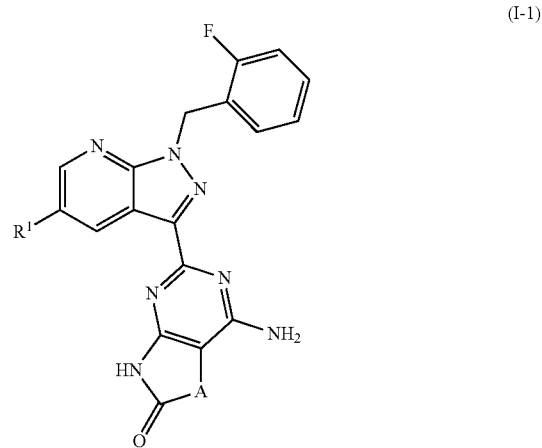

(I-1)

in which
A is $(C_1-C_3)$-alkanediyl or a group of the formula

where
* is the attachment site to the pyrimidine ring,
# is the attachment site to the carbonyl group,
the ring Q is a 4- to 6-membered heterocycle,
and
where $(C_1-C_3)$-alkanediyl may be substituted by 1 or 2 substituents independently selected from the group of fluorine, trifluoromethyl and $(C_1-C_4)$-alkyl,
$R^1$ is hydrogen or fluorine,
and the N-oxides, salts, solvates, salts of the N-oxides and solvates of the N-oxides or salts thereof.

Preference is also given in the context of the present invention to compounds of the formula (I) in which
A is a group of the formula

where
* is the attachment site to the pyrimidine ring,
# is the attachment site to the carbonyl group,
the ring Q is an azetidinyl, oxetanyl, pyrrolidinyl, tetrahydrofuranyl, piperidinyl or tetrahydropyranyl ring,
$R^1$ is hydrogen or fluorine,
$R^2$ is 2,2,2-trifluoroethyl, 3,3,3-trifluoroprop-1-yl, 4,4,4-trifluorobut-1-yl, 3,3,4,4,4-pentafluorobut-1-yl or benzyl,
where benzyl is substituted by 1 to 3 fluorine substituents,
and the salts, solvates and solvates of the salts thereof.

Preference is also given in the context of the present invention to compounds of the formula (I) in which
A is $(C_1-C_3)$-alkanediyl
where $(C_1-C_3)$-alkanediyl may be substituted by 1 or 2 substituents independently selected from the group of fluorine, $(C_1-C_4)$-alkyl, hydroxyl and amino,
and
where $(C_1-C_3)$-alkanediyl is substituted by 1 substituent selected from the group of fluorine and trifluoromethyl,
$R^1$ is hydrogen or fluorine,
$R^2$ is 2,2,2-trifluoroethyl, 3,3,3-trifluoroprop-1-yl, 4,4,4-trifluorobut-1-yl, 3,3,4,4,4-pentafluorobut-1-yl or benzyl,
where benzyl is substituted by 1 to 3 fluorine substituents,
and the salts, solvates and solvates of the salts thereof.

Preference is also given in the context of the present invention to compounds of the formula (I-1) in which
A is a group of the formula

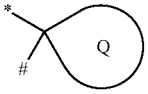

where
* is the attachment site to the pyrimidine ring,
# is the attachment site to the carbonyl group,
the ring Q is an azetidinyl, oxetanyl, pyrrolidinyl, tetrahydrofuranyl, piperidinyl or tetrahydropyranyl ring,
$R^1$ is hydrogen or fluorine,
and the salts, solvates and solvates of the salts thereof.

Preference is also given in the context of the present invention to compounds of the formula (I-1) in which
A is $(C_1-C_3)$-alkanediyl
where $(C_1-C_3)$-alkanediyl may be substituted by 1 or 2 substituents independently selected from the group of fluorine and $(C_1-C_4)$-alkyl,
and
where $(C_1-C_3)$-alkanediyl is substituted by 1 substituent selected from the group of fluorine and trifluoromethyl,
$R^1$ is hydrogen or fluorine,
and the salts, solvates and solvates of the salts thereof.

Preference is also given in the context of the present invention to compounds of the formula (I) in which
A is methylene or ethane-1,2-diyl,
where methylene and ethane-1,2-diyl are substituted by 1 or 2 substituents independently selected from the group of fluorine and trifluoromethyl,
and the salts, solvates and solvates of the salts thereof.

Preference is also given in the context of the present invention to compounds of the formula (I) in which
A is a group of the formula

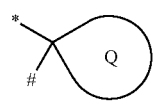

where
* is the attachment site to the pyrimidine ring,
# is the attachment site to the carbonyl group,
the ring Q is a 4- to 6-membered heterocycle,
and the salts, solvates and solvates of the salts thereof.

Preference is also given in the context of the present invention to compounds of the formula (I) in which
A is a group of the formula

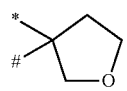

where
* is the attachment site to the pyrimidine ring,
# is the attachment site to the carbonyl group,
and the salts, solvates and solvates of the salts thereof.

Preference is also given in the context of the present invention to compounds of the formula (I) in which $R^1$ is fluorine.
and the salts, solvates and solvates of the salts thereof.

Preference is also given in the context of the present invention to compounds of the formula (I) in which
$R^2$ is 3,3,4,4,4-pentafluorobut-1-yl,
and the salts, solvates and solvates of the salts thereof.

Preference is also given in the context of the present invention to compounds of the formula (I) in which $R^2$ is benzyl, where benzyl is substituted by 1 to 3 fluorine substituents,
and the salts, solvates and solvates of the salts thereof.

Particular preference is given in the context of the present invention to the following compounds of the formula (I):

4-amino-2-[1-(2-fluorobenzyl)-1H-pyrazolo[3,4-b]pyridin-3-yl]-5,7-dihydro-6H-pyrrolo[2,3-d]pyrimidin-6-one 4-amino-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one 4-amino-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one 4'-amino-2'-[1-(2-fluorobenzyl)-1H-pyrazolo[3,4-b]pyridin-3-yl]-4,5-dihydrospiro[furan-3,5'-pyrrolo[2,3-d]pyrimidine]-6'(7'H)-one 4-amino-2-[1-(2-fluorobenzyl)-1H-pyrazolo[3,4-b]pyridin-3-yl]-5-methyl-5,8-dihydropyrido[2,3-d]pyrimidin-7(6H)-one 4-amino-2-[1-(2-fluorobenzyl)-1H-pyrazolo[3,4-b]pyridin-3-yl]-5-(trifluoromethyl)-5,8-dihydropyrido[2,3-d]pyrimidin-7(6H)-one 4-amino-5,5-dimethyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one 4-amino-2-[5-fluoro-1-(3,3,4,4,4-pentafluorobutyl)-1H-pyrazolo[3,4-b]pyridin-3-yl]-5,5-dimethyl-5,7-dihydro-6H-pyrrolo[2,3-d]pyrimidin-6-one Special preference is given in the context of the present invention to the following compounds of the formula (I):

4'-amino-2'-[1-(2-fluorobenzyl)-1H-pyrazolo[3,4-b]pyridin-3-yl]-4,5-dihydrospiro[furan-3,5'-pyrrolo[2,3-d]pyrimidine]-6'(7'H)-one 4-amino-2-[1-(2-fluorobenzyl)-1H-pyrazolo[3,4-b]pyridin-3-yl]-5-(trifluoromethyl)-5,8-dihydropyrido[2,3-d]pyrimidin-7(6H)-one The individual radical definitions specified in the respective combinations or preferred combinations of radicals are, independently of the respective combinations of the radicals specified, also replaced as desired by radical definitions of other combinations.

Particular preference is given to combinations of two or more of the preferred ranges mentioned above.

The invention further provides a process for preparing the inventive compounds of the formula (I), characterized in that

[A] a compound of the formula (II)

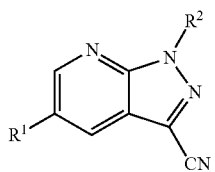

in which $R^1$ and $R^2$ are each as defined above
is converted under acidic conditions to a compound of the formula (III)

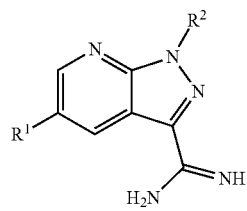

in which $R^1$ and $R^2$ are each as defined above,
the latter is reacted in an inert solvent in the presence of a suitable base with a compound of the formula (IV)

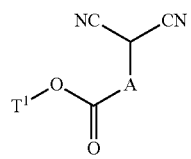

in which A is as defined above and
$T^1$ is $(C_1-C_4)$-alkyl,
to give a compound of the formula (I)

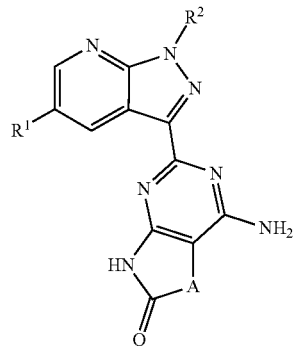

in which A, $R^1$ and $R^2$ are each as defined above, or

[B] a compound of the formula (III) is reacted in an inert solvent in the presence of a suitable base with a compound of the formula (V)

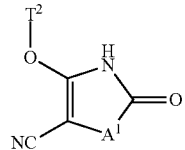

in which
$A^1$ is $(C_2-C_3)$-alkanediyl,
where $(C_2-C_3)$-alkanediyl may be substituted by 1 or 2 substituents independently selected from the group of fluorine, trifluoromethyl and $(C_1-C_4)$-alkyl, in which ($C_1$-$C_4$)-alkyl may be substituted by 1 to 3 substituents independently selected from the group of fluorine, trifluoromethyl and hydroxyl, and $T^2$ is ($C_1$-$C_4$)-alkyl, to give a compound of the formula (I-A)

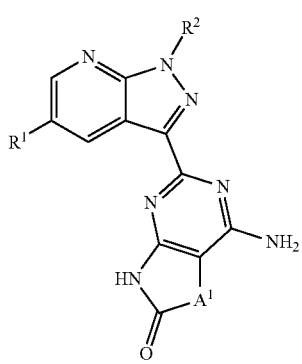

(I-A)

in which $A^1$, $R^1$ and $R^2$ are each as defined above, the resulting compounds of the formulae (I) and (I-A) are optionally converted with the appropriate (i) solvents and/or (ii) acids or bases to the solvates, salts and/or solvates of the salts thereof.

The conversion of (II)→(III) is effected by the methods known to those skilled in the art in a two-stage process, first forming the imino ester with sodium methoxide in methanol at 0° C. to +40° C., followed by nucleophilic addition of an ammonia equivalent, for example ammonia or ammonium chloride, in a suitable acid to form the amidine (III) at +50 to +150° C.

Suitable acids for the formation of the amidine (III) are inorganic acids, for example hydrogen chloride/hydrochloric acid, sulfuric acid, polyphosphoric acid or phosphoric acid, or organic acids, for example acetic acid, trifluoroacetic acid or formic acid. Preference is given to using hydrochloric acid or acetic acid.

Inert solvents for the process step (III)+(IV)→(I) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine, acetonitrile or else water. It is likewise possible to use mixtures of the solvents mentioned. Preference is given to tert-butanol.

Suitable bases for the process step (III)+(IV)→(I) are alkali metal hydroxides, for example lithium, sodium or potassium hydroxide, alkali metal carbonates such as lithium, sodium, potassium or cesium carbonate, alkali metal hydrogencarbonates such as sodium or potassium hydrogencarbonate, alkali metal alkoxides such as sodium or potassium methoxide, sodium or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to potassium tert-butoxide.

The reaction (III)+(IV)→(I) is generally performed within a temperature range from +20° C. to +150° C., preferably at +75° C. to +100° C., optionally in a microwave. The reaction can be effected at standard, elevated or reduced pressure (for example from 0.5 to 5 bar). In general, standard pressure is employed.

Inert solvents for the process step (III)+(V)→(1-A) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine, acetonitrile or else water. It is likewise possible to use mixtures of the solvents mentioned.

Suitable bases for the process step (III)+(V)→(I-A) are alkali metal hydroxides, for example lithium, sodium or potassium hydroxide, alkali metal carbonates such as lithium, sodium, potassium or cesium carbonate, alkali metal hydrogencarbonates such as sodium or potassium hydrogencarbonate, alkali metal alkoxides such as sodium or potassium methoxide, sodium or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN).

Preference is given to using sodium methoxide in methanol or potassium tert-butoxide in tert-butanol.

The reaction (III)+(V)→(I-A) is generally performed within a temperature range from +20° C. to +150° C., preferably at +60° C. to +100° C., optionally in a microwave. The reaction can be effected at standard, elevated or reduced pressure (for example from 0.5 to 5 bar). In general, standard pressure is employed.

The processes described above are illustrated by way of example with reference to the following synthesis schemes (Schemes 1 and 2):

Scheme 1

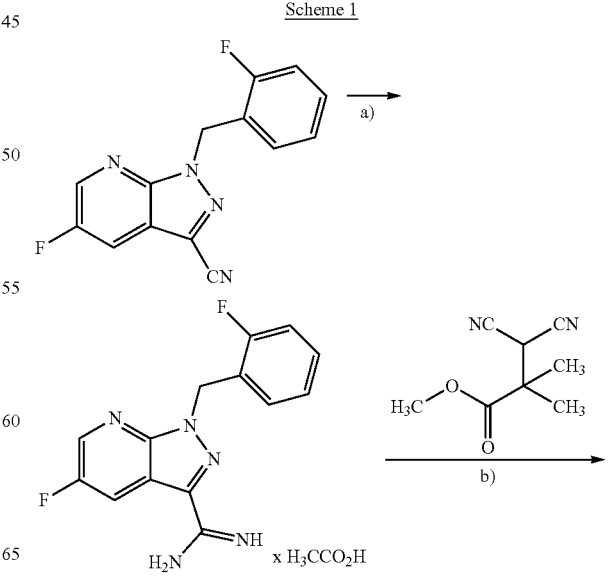

-continued

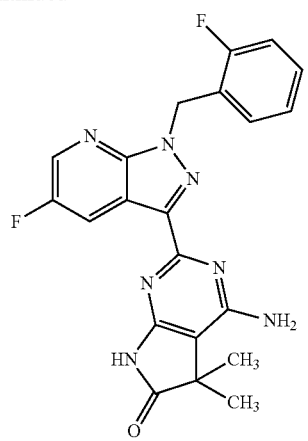

[a]: 1. sodium methoxide, methanol 2. ammonium chloride, acetic acid; b): KOt-Bu, t-BuOH].

Scheme 2:

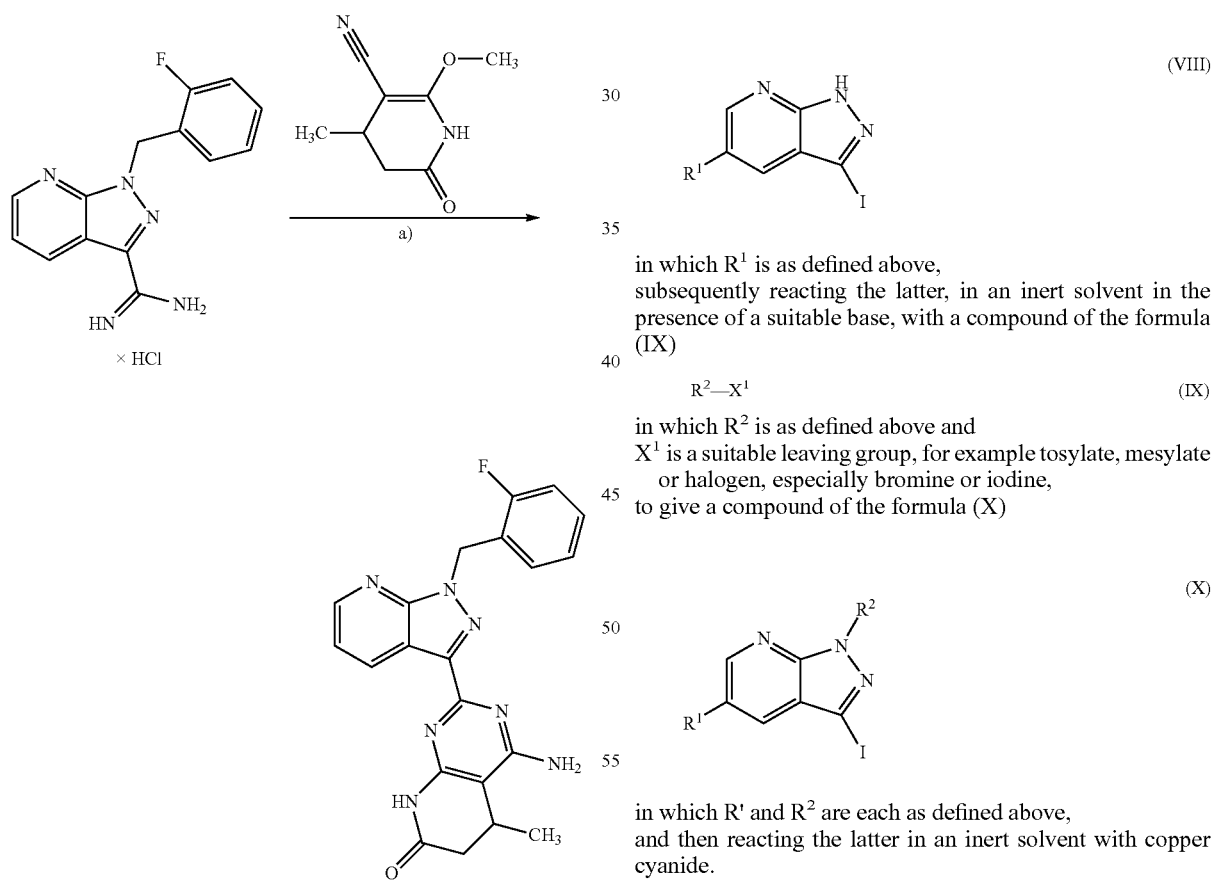

[a]: NaOMe, methanol, 65° C.].

The compounds of the formula (II) are known from the literature (see, for example, WO 03/095451, example 4A) or can be prepared by cyclizing a compound of the formula (VI)

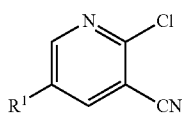

in which R' is as defined above
in an inert solvent with hydrazine hydrate to give a compound of the formula (VII)

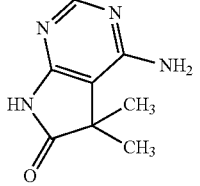

in which R' is as defined above,
then reacting the latter, in an inert solvent in the presence of a suitable Lewis acid, first with isopentyl nitrite to give the corresponding diazonium salt, and then converting the latter directly with sodium iodide to a compound of the formula (VIII)

in which $R^1$ is as defined above,
subsequently reacting the latter, in an inert solvent in the presence of a suitable base, with a compound of the formula (IX)

$$R^2\text{—}X^1 \quad (IX)$$

in which $R^2$ is as defined above and
$X^1$ is a suitable leaving group, for example tosylate, mesylate or halogen, especially bromine or iodine,
to give a compound of the formula (X)

(X)

in which R' and $R^2$ are each as defined above,
and then reacting the latter in an inert solvent with copper cyanide.

Inert solvents for the process step (VI)→(VII) are alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine, acetonitrile or else water. It is likewise possible to use mixtures of the solvents mentioned. Preference is given to 1,2-ethanediol.

The reaction (VI)→(VII) is generally performed within a temperature range from +60° C. to +200° C., preferably at +120° C. to +180° C. The reaction can be effected at standard, elevated or reduced pressure (for example from 0.5 to 5 bar). In general, standard pressure is employed.

Inert solvents for the reaction (VII)→(VIII) are, for example, halohydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, or other solvents such as dimethylformamide (DMF), dimethyl sulfoxide (DMSO), N,N'-dimethylpropyleneurea (DMPU), N-methylpyrrolidone (NMP), pyridine or acetonitrile. Preference is given to DMF.

Suitable Lewis acids for the process step (VII)→(VIII) are boron trifluoride-diethyl ether complex, cerium(IV) ammonium nitrate (CAN), tin(II) chloride, lithium perchlorate, zinc (II) chloride, indium(III) chloride or indium(III) bromide. Preference is given to boron trifluoride-diethyl ether complex.

The reaction (VII)→(VIII) is generally performed within a temperature range from −78° C. to +40° C., preferably at 0° C. to +20° C. The reaction can be effected at standard, elevated or reduced pressure (for example from 0.5 to 5 bar). In general, standard pressure is employed.

Inert solvents for the reaction (VIII)+(IX)→(X) are, for example, halohydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, or other solvents such as dimethylformamide (DMF), dimethyl sulfoxide (DMSO), N,N'-dimethylpropyleneurea (DMPU), N-methylpyrrolidone (NMP), pyridine, acetonitrile. Preference is given to DMF.

Suitable bases for the process step (VIII)+(IX)→(X) are alkali metal hydrides such as potassium hydride or sodium hydride, alkali metal carbonates such as lithium, sodium, potassium or cesium carbonate, alkali metal hydrogencarbonates such as sodium or potassium hydrogencarbonate, alkali metal alkoxides such as sodium or potassium methoxide, sodium or potassium ethoxide or potassium tert-butoxide, amides such as sodium amide, lithium, sodium or potassium bis(trimethylsilyl)amide or lithium diisopropylamide, organometallic compounds such as butyllithium or phenyllithium, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to cesium carbonate.

The reaction (VIII)+(IX)→(X) is generally performed within a temperature range from 0° C. to +60° C., preferably at +10° C. to +25° C. The reaction can be effected at standard, elevated or reduced pressure (for example from 0.5 to 5 bar). In general, standard pressure is employed.

Inert solvents for the process step (X)→(II) are, for example, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine or acetonitrile. It is likewise possible to use mixtures of the solvents mentioned. Preference is given to DMSO.

The reaction (X)→(II) is generally performed within a temperature range from +20° C. to +180° C., preferably at +100° C. to +160° C., optionally in a microwave. The reaction can be effected at standard, elevated or reduced pressure (for example from 0.5 to 5 bar). In general, standard pressure is employed.

The preparation process described can be illustrated by way of example by the following synthesis scheme (Scheme 3):

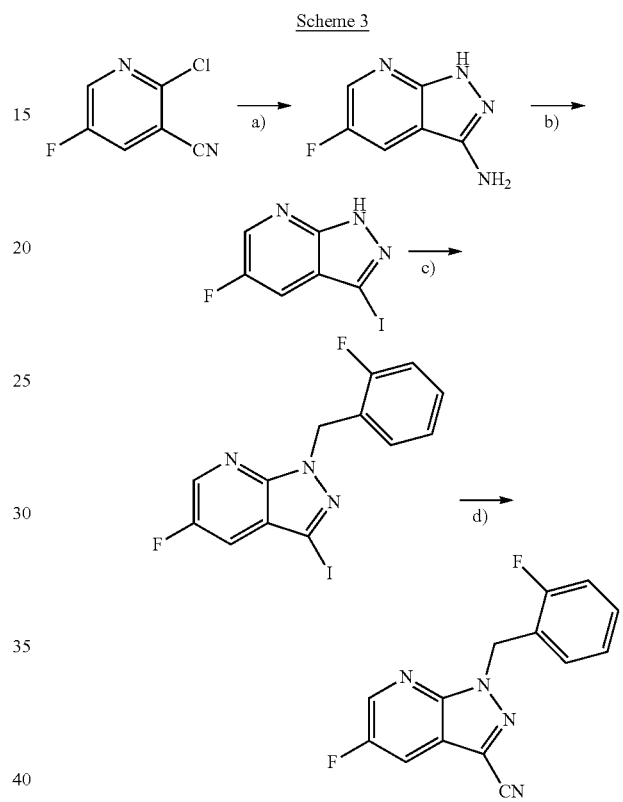

[a]: hydrazine hydrate, 1,2-ethanediol; b): isopentyl nitrite, NaI, THF; b): 2-fluorobenzyl bromide, $Cs_2CO_3$, DMF; d): CuCN, DMSO].

The compound of the formula (VI) is known from the literature [cf., for example, Winn M., J. Med. Chem. 1993, 36, 2676-7688; EP 634 413-A1; CN 1613849-A; EP 1626045-A1; WO 2009/018415], or can be prepared in analogy to processes known from the literature or as shown in the following synthesis scheme (Scheme 4):

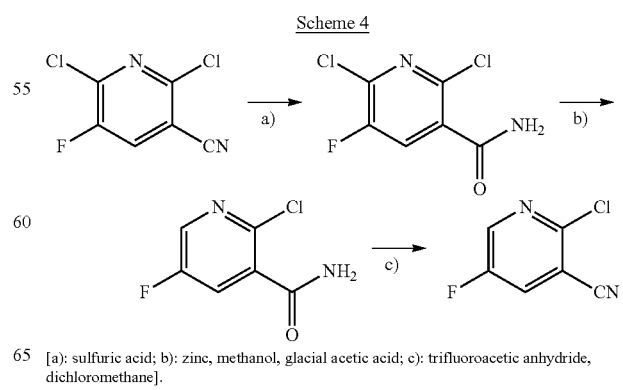

[a]: sulfuric acid; b): zinc, methanol, glacial acetic acid; c): trifluoroacetic anhydride, dichloromethane].

The compounds of the formulae (IV) and (V) are commercially available and are known from the literature, and can be prepared in analogy to processes known from the literature or as shown by way of example in the following synthesis schemes (Schemes 5 and 6):

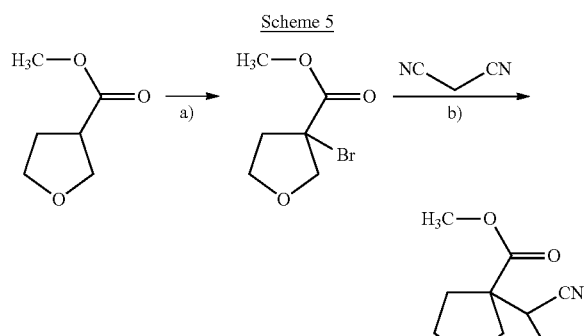

[a]: 1. LiHMDS, -78° C., THF, 2. NBS; b): NaH, 50° C., THF].

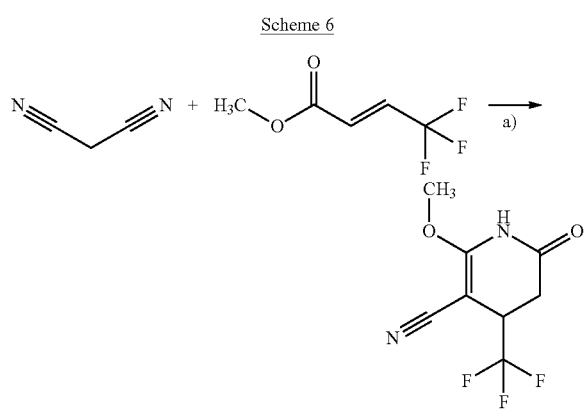

[a]: NaOMe, MeOH, 65° C.].

The inventive compounds are potent stimulators of soluble guanylate cyclase, have valuable pharmacological properties and are therefore suitable for treatment and/or prophylaxis of disorders in humans and animals.

The inventive compounds cause vasorelaxation and inhibition of platelet aggregation, and lead to a decrease in blood pressure and to a rise in coronary blood flow. These effects are mediated by direct stimulation of soluble guanylate cyclase and an intracellular rise in cGMP. In addition, the inventive compounds enhance the action of substances which increase the cGMP level, for example EDRF (endothelium-derived relaxing factor), NO donors, protoporphyrin IX, arachidonic acid or phenylhydrazine derivatives.

The inventive compounds are suitable for treatment and/or prophylaxis of cardiovascular, pulmonary, thromboembolic and fibrotic disorders.

The inventive compounds can therefore be used in medicaments for treatment and/or prophylaxis of cardiovascular disorders, for example hypertension, acute and chronic heart failure, coronary heart disease, stable and unstable angina pectoris, peripheral and cardiovascular disorders, arrhythmias, atrial and ventricular arrhythmias and impaired conduction, for example atrioventricular grade I-III blocks (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, Sick-Sinus syndrome, syncopes, AV-nodal re-entry tachycardia, Wolff-Parkinson-White syndrome, acute coronary syndrome (ACS), autoimmune cardiac disorders (pericarditis, endocarditis, valvolitis, aortitis, cardiomyopathies), shock such as cardiogenic shock, septic shock and anaphylactic shock, aneurisms, boxer cardiomyopathy (premature ventricular contraction (PVC)), for treatment and/or prophylaxis of thromboembolic disorders and ischemias such as myocardial ischemia, myocardial infarction, stroke, cardiac hypertrophy, transient and ischemic attacks, preeclampsia, inflammatory cardiovascular disorders, spasms of the coronary arteries and peripheral arteries, edema formation, for example pulmonary edema, cerebral edema, renal edema or edema caused by heart failure, impaired peripheral perfusion, reperfusion damage, arterial and venous thromboses, microalbuminuria, myocardial insufficiency, endothelial dysfunction, for prevention of restenoses, such as after thrombolysis treatments, percutaneous transluminal angioplasties (PTA), transluminal coronary angioplasties (PTCA), heart transplants and bypass operations, and micro- and macrovascular damage (vasculitis), elevated levels of fibrinogen and of low-density LDL, and elevated concentrations of plasminogen activator inhibitor 1 (PAI-1), and for treatment and/or prophylaxis of erectile dysfunction and female sexual dysfunction.

In the context of the present invention, the term "heart failure" also encompasses more specific or related types of disease, such as acute decompensated heart failure, right heart failure, left heart failure, global failure, ischemic cardiomyopathy, dilated cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure.

In addition, the inventive compounds can also be used for treatment and/or prophylaxis of arteriosclerosis, disturbed lipid metabolism, hypolipoproteinemias, dyslipidemias, hypertriglyceridemias, hyperlipidemias, hypercholesterolemias, abetalipoproteinemias, sitosterolemia, xanthomatosis, Tangier disease, adiposity, obesity and combined hyperlipidemias, and also of metabolic syndrome.

Moreover, the inventive compounds can be used for treatment and/or prophylaxis of primary and secondary Raynaud's phenomenon, of microcirculation disorders, claudication, peripheral and autonomic neuropathies, diabetic microangiopathies, diabetic retinopathy, diabetic ulcers at the extremities, gangrene, CREST syndrome, erythematosis, onychomycosis, rheumatic disorders, and for promotion of wound healing.

Furthermore, the inventive compounds are suitable for treatment of urological disorders, for example benign prostate syndrome (BPS), benign prostate hyperplasia (BPH), benign prostate enlargement (BPE), bladder outlet obstruction (BOO), lower urinary tract syndrome (LUTS, including feline urological syndrome (FUS)), disorders of the urogenital system including neurogenic overactive bladder (OAB) and (IC), incontinence (UI), for example mixed, urge, stress or overflow incontinence (MUI, UUI, SUI, OUI), pelvic pain, benign and malignant disorders of the organs in the male and female urogenital systems.

Furthermore, the inventive compounds are suitable for treatment and/or prophylaxis of renal disorders, especially of acute and chronic renal insufficiency, and of acute and chronic kidney failure. In the context of the present invention, the term "renal insufficiency" encompasses both acute and chronic manifestations of renal insufficiency, and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example, by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the inventive compounds for treatment and/or prophylaxis of sequelae of renal insufficiency, for example pulmonary edema, heart failure, uremia, anemia, electrolyte disturbances (for example hypercalemia, hyponatremia) and disturbances in bone and carbohydrate metabolism.

Furthermore, the inventive compounds are also suitable for treatment and/or prophylaxis of asthmatic disorders, pulmonary arterial hypertension (PAH) and other forms of pulmonary hypertension (PH) including pulmonary hypertension associated with left heart disease, HIV, sickle cell anemia, thromboembolisms (CTEPH), sarcoidosis, COPD or pulmonary fibrosis, of chronic-obstructive pulmonary disease (COPD), acute respiratory distress syndrome (ARDS), acute lung injury (ALI), alpha-1 antitrypsin deficiency (AATD), pulmonary fibrosis, pulmonary emphysema (for example pulmonary emphysema induced by cigarette smoke) and cystic fibrosis (CF).

The compounds described in the present invention are also active ingredients for control of central nervous system disorders characterized by disturbances of the NO/cGMP system. More particularly, they are suitable for improving perception, concentration, learning or memory after cognitive impairments such as those occurring particularly in the event of situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children having learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelination, multiple sclerosis, thalamic degeneration, Creutzfeld-Jacob dementia, HIV dementia, schizophrenia with dementia or Korsakoff's psychosis. They are also suitable for treatment and/or prophylaxis of central nervous system disorders such as states of anxiety, tension and depression, CNS-related sexual dysfunction and disrupted sleep, and for control of pathological disturbances of the intake of food, stimulants and addictive substances.

Furthermore, the inventive compounds are also suitable for regulation of cerebral blood flow and are thus effective agents for control of migraine. They are also suitable for prophylaxis and control of sequalae of cerebral infarct (Apoplexia cerebri) such as stroke, cerebral ischemia and skull-brain trauma. The inventive compounds can likewise be used to control states of pain and tinnitus.

Moreover, the inventive compounds have antiinflammatory action and can therefore be used as antiinflammatories for treatment and/or prophylaxis of sepsis (SIRS), multiple organ failure (MODS, MOF), inflammatory disorders of the kidney, chronic bowel inflammation (IBD, Crohn's Disease, UC), pancreatitis, peritonitis, rheumatoid disorders, inflammatory skin disorders and inflammatory eye disorders.

In addition, the inventive compounds can likewise be used for treatment and/or prophylaxis of autoimmune disorders.

Furthermore, the inventive compounds are suitable for treatment and/or prophylaxis of fibrotic disorders of the internal organs, for example of the lung, of the heart, of the kidneys, of the bone marrow and especially of the liver, and also of dermatological fibroses and fibrotic disorders of the eye. In the context of the present inventions, the term "fibrotic disorders" encompasses especially the following terms: hepatic fibrosis, hepatic cirrhosis, pulmonary fibrosis, endomyocardial fibrosis, nephropathy, glomerulonephritis, interstitial renal fibrosis, fibrotic damage resulting from diabetes, myelofibrosis and similar fibrotic disorders, scleroderma, morphea, keloids, hypertrophic scarring including after surgical procedures, naevi, diabetic retinopathy, proliferative vitreoretinopathy and disorders of the connective tissue (for example sarcoidosis).

Furthermore, the inventive compounds are suitable for control of postoperative scarring, for example resulting from glaucoma operations.

The inventive compounds can likewise be used cosmetically, in the event of ageing and keratinized skin.

Moreover, the inventive compounds are suitable for treatment and/or prophylaxis of hepatitis, neoplasms, osteoporosis, glaucoma and gastroparesis.

The present invention further provides for the use of the inventive compounds for treatment and/or prophylaxis of disorders, especially of the aforementioned disorders.

The present invention further provides for the use of the inventive compounds for treatment and/or prophylaxis of heart failure, angina pectoris, hypertension, pulmonary hypertension, ischemia, vascular disorders, renal insufficiency, thromboembolic disorders, fibrotic disorders and arteriosclerosis.

The present invention further provides the inventive compounds for use in a method for treatment and/or prophylaxis of heart failure, angina pectoris, hypertension, pulmonary hypertension, ischemia, vascular disorders, renal insufficiency, thromboembolic disorders, fibrotic disorders and arteriosclerosis.

The present invention further provides for the use of the inventive compounds for production of a medicament for treatment and/or prophylaxis of disorders, especially of the aforementioned disorders.

The present invention further provides for the use of the inventive compounds for production of a medicament for treatment and/or prophylaxis of heart failure, angina pectoris, hypertension, pulmonary hypertension, ischemia, vascular disorders, renal insufficiency, thromboembolic disorders, fibrotic disorders and arteriosclerosis.

The present invention further provides a method for treatment and/or prophylaxis of disorders, especially of the aforementioned disorders, using an effective amount of at least one of the inventive compounds.

The present invention further provides a method for treatment and/or prophylaxis of heart failure, angina pectoris, hypertension, pulmonary hypertension, ischemia, vascular disorders, renal insufficiency, thromboembolic disorders, fibrotic disorders and arteriosclerosis using an effective amount of at least one of the inventive compounds.

The inventive compounds can be used alone or, if required, in combination with other active ingredients. The present invention further provides medicaments comprising at least one of the inventive compounds and one or more further active ingredients, especially for treatment and/or prophylaxis of the aforementioned disorders. Preferred examples of suitable active ingredient combinations include:

organic nitrates and NO donors, for example sodium nitroprusside, nitroglycerine, isosorbide mononitrate, isosorbide dinitrate, molsidomine or SIN-1, and inhaled NO;

compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil;

antithrombotic agents, by way of example and with preference from the group of the platelet aggregation inhibitors, the anticoagulants or the profibrinolytic substances;

hypotensive active ingredients, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or active ingredients which modify lipid metabolism, by way of example and with preference from the group of the thyroid receptor agonists, cholesterol synthesis inhibitors, by way of example and with preference HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Antithrombotic agents are preferably understood to mean compounds from the group of the platelet aggregation inhibitors, the anticoagulants or the profibrinolytic substances.

In a preferred embodiment of the invention, the inventive compounds are administered in combination with a platelet aggregation inhibitor, by way of example and with preference aspirin, clopidogrel, ticlopidin or dipyridamole.

In a preferred embodiment of the invention, the inventive compounds are administered in combination with a thrombin inhibitor, by way of example and with preference ximelagatran, dabigatran, melagatran, bivalirudin or clexane.

In a preferred embodiment of the invention, the inventive compounds are administered in combination with a GPIIb/IIIa antagonist, by way of example and with preference tirofiban or abciximab.

In a preferred embodiment of the invention, the inventive compounds are administered in combination with a factor Xa inhibitor, by way of example and with preference rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the inventive compounds are administered in combination with heparin or with a low molecular weight (LMW) heparin derivative.

In a preferred embodiment of the invention, the inventive compounds are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists and the diuretics.

In a preferred embodiment of the invention, the inventive compounds are administered in combination with a calcium antagonist, by way of example and with preference nifedipine, amlodipine, verapamil or diltiazem.

In a preferred embodiment of the invention, the inventive compounds are administered in combination with an alpha-1-receptor blocker, by way of example and with preference prazosin.

In a preferred embodiment of the invention, the inventive compounds are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the inventive compounds are administered in combination with an angiotensin AII antagonist, by way of example and with preference losartan, candesartan, valsartan, telmisartan or embursatan.

In a preferred embodiment of the invention, the inventive compounds are administered in combination with an ACE inhibitor, by way of example and with preference enalapril, captopril, lisinopril, ramipril, delapril, fosinopril, quinopril, perindopril or trandopril.

In a preferred embodiment of the invention, the inventive compounds are administered in combination with an endothelin antagonist, by way of example and with preference bosentan, darusentan, ambrisentan or sitaxsentan.

In a preferred embodiment of the invention, the inventive compounds are administered in combination with a renin inhibitor, by way of example and with preference aliskiren, SPP-600 or SPP-800.

In a preferred embodiment of the invention, the inventive compounds are administered in combination with a mineralocorticoid receptor antagonist, by way of example and with preference spironolactone or eplerenone.

In a preferred embodiment of the invention, the inventive compounds are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Agents which modify lipid metabolism are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein (a) antagonists.

In a preferred embodiment of the invention, the inventive compounds are administered in combination with a CETP inhibitor, by way of example and with preference dalcetrapib, BAY 60-5521, anacetrapib oder CETP vaccine (CETi-1).

In a preferred embodiment of the invention, the inventive compounds are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the inventive compounds are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the inventive compounds are administered in combination with a squalene synthesis inhibitor, by way of example and with preference BMS-188494 or TAK-475.

In a preferred embodiment of the invention, the inventive compounds are administered in combination with an ACAT inhibitor, by way of example and with preference avasimibe, melinamide, pactimibe, eflucimibe or SMP-797.

In a preferred embodiment of the invention, the inventive compounds are administered in combination with an MTP inhibitor, by way of example and with preference implitapide, BMS-201038, R-103757 or JTT-130.

In a preferred embodiment of the invention, the inventive compounds are administered in combination with a PPAR-gamma agonist, by way of example and with preference pioglitazone or rosiglitazone.

In a preferred embodiment of the invention, the inventive compounds are administered in combination with a PPAR-delta agonist, by way of example and with preference GW 501516 or BAY 68-5042.

In a preferred embodiment of the invention, the inventive compounds are administered in combination with a cholesterol absorption inhibitor, by way of example and with preference ezetimibe, tiqueside or pamaqueside.

In a preferred embodiment of the invention, the inventive compounds are administered in combination with a lipase inhibitor, by way of example and with preference orlistat.

In a preferred embodiment of the invention, the inventive compounds are administered in combination with a polymeric bile acid adsorbent, by way of example and with preference cholestyramine, colestipol, colesolvam, CholestaGel or colestimide.

In a preferred embodiment of the invention, the inventive compounds are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the inventive compounds are administered in combination with a lipoprotein (a) antagonist, by way of example and with preference gemcabene calcium (CI-1027) or nicotinic acid.

The present invention further provides medicaments which comprise at least one inventive compound, typically together with one or more inert, nontoxic, pharmaceutically suitable excipients, and for the use thereof for the aforementioned purposes.

The inventive compounds may act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The inventive compounds can be administered in administration forms suitable for these administration routes.

Suitable administration forms for oral administration are those which work according to the prior art, which release the inventive compounds rapidly and/or in a modified manner and which contain the inventive compounds in crystalline and/or amorphized and/or dissolved form, for example tablets (uncoated or coated tablets, for example with gastric juice-resistant or retarded-dissolution or insoluble coatings which control the release of the inventive compound), tablets or films/oblates which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral or parenteral administration is preferred, especially oral administration.

The inventive compounds can be converted to the administration forms mentioned. This can be done in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavor and/or odor correctors.

In general, it has been found to be advantageous in the case of parenteral administration to administer amounts of from about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight.

It may nevertheless be necessary in some cases to deviate from the stated amounts, specifically as a function of the body weight, route of administration, individual response to the active ingredient, nature of the preparation and time or interval over which administration takes place. Thus, in some cases less than the abovementioned minimum amount may be sufficient, while in other cases the upper limit mentioned must be exceeded. In the case of administration of relatively large amounts, it may be advisable to divide these into several individual doses over the course of the day.

The working examples which follow illustrate the invention. The invention is not restricted to the examples.

The percentages in the tests and examples which follow are, unless stated otherwise, percentages by weight; parts are parts by weight. Solvent ratios, dilution ratios and concentration figures for liquid/liquid solutions are each based on volume.

A. EXAMPLES

Abbreviations and Acronyms
aq. aqueous solution
calc. calculated
DCI direct chemical ionization (in MS)
DMF dimethylformamide
DMSO dimethyl sulfoxide
eq. equivalent(s)
ESI electrospray ionization (in MS)
Et ethyl
h hour(s)
HPLC high-pressure, high-performance liquid chromatography
HRMS high-resolution mass spectrometry
conc. concentrated
LC/MS liquid chromatography-coupled mass spectrometry
LiHMDS lithium hexamethyldisilazide
Me methyl
min minute(s)
MS mass spectrometry
NMR nuclear magnetic resonance spectroscopy
$Pd_2 dba_3$ tris(dibenzylideneacetone)dipalladium
Ph phenyl
RT room temperature
$R_t$ retention time (in HPLC)
t-Bu tert-butyl
THF tetrahydrofuran
UV ultraviolet spectrometry
v/v volume to volume ratio (of a solution)
XPHOS dicyclohexyl(2',4',6'-triisopropylbiphenyl-2-yl)phosphine LC/MS Methods:

Method 1 (LC-MS):
Instrument: Waters ACQUITY SQD UPLC System; column: Waters Acquity UPLC HSS T3 1.8μ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 210-400 nm.

Method 2 (LC-MS):
MS instrument: Waters ZQ; HPLC instrument: Agilent 1100 Series; UV DAD; column: Thermo Hypersil GOLD 3μ 20 mm×4 mm; eluent A: 1 l water+0.5 ml 50% formic acid, eluent B: 1 l acetonitrile+0.5 ml 50% formic acid; gradient: 0.0 min 100% A→3.0 min 10% A→4.0 min 10% A; oven: 55° C.; flow rate: 2 ml/min; UV detection: 210 nm.

Method 3 (LC-MS):
Instrument: Waters ACQUITY SQD UPLC System; column: Waters Acquity UPLC HSS T3 1.8μ 30×2 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A oven: 50° C.; flow rate: 0.60 ml/min; UV detection: 208-400 nm.

Starting Compounds and Intermediates

Example 1A 1-(2-fluorobenzyl)-1H-pyrazolo[3,4-b]pyridin-3-carboximidamide hydrochloride

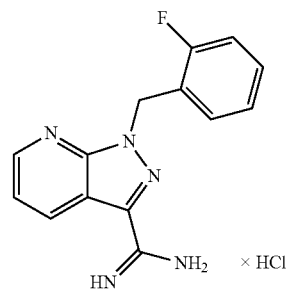 [SMILES: N=C(N)c1nn(Cc2ccccc2F)c2ncccc12]

The synthesis of this compound is described in WO 2003/095451, example 6A.

Example 2A 2,6-dichloro-5-fluoronicotinamide

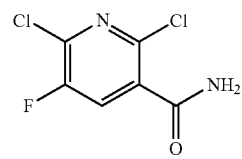 [SMILES: NC(=O)c1cc(F)c(Cl)nc1Cl]

A suspension of 25 g (130.90 mmol) of 2,6-dichloro-5-fluoro-3-cyanopyridine in conc. sulfuric acid (125 ml) was stirred at 60-65° C. for 1 h. After cooling to RT, the contents of the flask were poured onto ice-water and extracted three times with ethyl acetate (100 ml each time). The combined organic phases were washed with water (100 ml) and then with saturated aqueous sodium hydrogencarbonate solution (100 ml), dried and concentrated on a rotary evaporator. The material obtained was dried under high vacuum.

Yield: 24.5 g (90% of theory)

$^1$H NMR (400 MHz, DMSO-$d_6$): δ=7.95 (br s, 1H), 8.11 (br s, 1H), 8.24 (d, 1H).

Example 3A 2-chloro-5-fluoronicotinamide

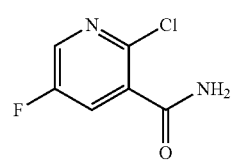 [SMILES: NC(=O)c1cc(F)cnc1Cl]

A suspension of 21.9 g (335.35 mmol) of zinc in methanol (207 ml) was admixed at RT with 44 g (210.58 mmol) of 2,6-dichloro-5-fluoronicotinamide. Acetic acid (18.5 ml) was then added, and the mixture was heated to reflux while stirring for 24 h. The contents of the flask were then decanted off from the zinc, and ethyl acetate (414 ml) and saturated aqueous sodium hydrogencarbonate solution (414 ml) were added, followed by vigorous stirring. Subsequently, the reaction mixture was filtered with suction through kieselguhr and washed through three times with ethyl acetate (517 ml each time). The organic phase was removed and the aqueous phase was washed with ethyl acetate (258 ml). The combined organic phases were washed once with saturated aqueous sodium hydrogencarbonate solution (414 ml), dried and concentrated under reduced pressure. Dichloromethane (388 ml) was added to the crystals thus obtained, and the mixture was stirred for 20 min. The mixture was once more filtered with suction, washed through with diethyl ether and sucked dry.

Yield: 20.2 g (53% of theory)

$^1$H NMR (400 MHz, DMSO-$d_6$): δ=7.87 (br s, 1H), 7.99 (dd, 1H), 8.10 (br s, 1H), 8.52 (d, 1H).

Example 4A 2-chloro-5-fluoronicotinonitrile

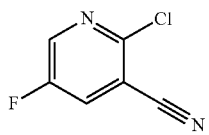

81.2 ml (582.25 mmol) of triethylamine were added to a suspension of 46.2 g (264.66 mmol) of 2-chloro-5-fluoronicotinamide in dichloromethane (783 ml), and the mixture was cooled to 0° C. Then, while stirring, 41.12 ml (291.13 mmol) of trifluoroacetic anhydride were slowly added dropwise and the mixture was stirred at 0° C. for 1.5 h. The reaction solution was subsequently washed twice with saturated aqueous sodium hydrogencarbonate solution (391 ml each time), dried and concentrated under reduced pressure.

Yield: 42.1 g (90% of theory).

$^1$H NMR (400 MHz, DMSO-$d_6$): δ=8.66 (dd, 1H), 8.82 (d, 1H).

Example 5A 5-fluoro-1H-pyrazolo[3,4-b]pyridine-3-amine

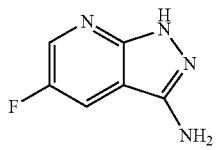 [SMILES: Nc1n[nH]c2ncc(F)cc12]

A suspension of 38.5 g (245.93 mmol) of 2-chloro-5-fluoronicotinonitrile was initially charged in 1,2-ethanediol (380 ml), and hydrazine hydrate (119.6 ml, 2.459 mol) was then added. The mixture was heated under reflux while stirring for 4 h. The product precipitated in the course of cooling. Water (380 ml) was added to the yellow crystals, and the mixture was stirred at RT for 10 min. The suspension was then filtered with suction through a frit and washed through with water (200 ml) and with THF at −10° C. (200 ml). The residue was dried under high vacuum over phosphorus pentoxide.

Yield: 22.8 g (61% of theory)

$^1$H NMR (400 MHz, DMSO-$d_6$): δ=5.54 (s, 2H), 7.96 (dd, 1H), 8.38 (m, 1H), 12.07 (m, 1H).

Example 6A 5-fluoro-3-iodo-1H-pyrazolo[3,4-b]pyridine

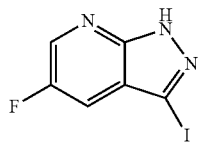

10 g (65.75 mmol) of 5-fluoro-1H-pyrazolo[3,4-b]pyridine-3-amine were initially charged in THF (329 ml), and the mixture was cooled to 0° C. 16.65 ml (131.46 mmol) of boron trifluoride diethyl ether complex were then added gradually. The reaction mixture was cooled further to −10° C. A solution of 10.01 g (85.45 mmol) of isopentyl nitrite in THF (24.39 ml) was then added gradually, and the mixture was stirred for a further 30 min. The mixture was diluted with cold diethyl ether (329 ml) and the resulting solid was filtered off. The diazonium salt thus prepared was added in portions to a solution at 0° C. of 12.81 g (85.45 mmol) of sodium iodide in acetone (329 ml), and the mixture was stirred at RT for 30 min. The reaction mixture was poured onto ice-water (1.8 l) and extracted twice with ethyl acetate (487 ml each time). The collected organic phases were washed with saturated aqueous sodium chloride solution (244 ml), dried, filtered and concentrated. This gave 12.1 g (86% purity, 60% of theory) of the desired compound in solid form. The crude product was converted without further purification.

LC-MS (method 1): $R_t$=1.68 min; MS (ESIpos): m/z=264 (M+H)$^+$

Example 7A 5-fluoro-1-(2-fluorobenzyl)-3-iodo-1H-pyrazolo[3,4-b]pyridine

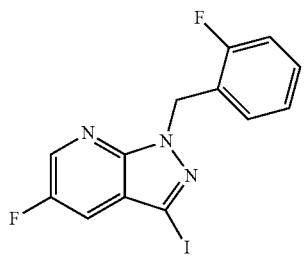 [SMILES: Fc1cnc2c(c1)c(I)nn2Cc1ccccc1F]

12.1 g (39.65 mmol) of the compound from Example 6A were initially charged in DMF (217 ml), and 8.25 g (43.62 mmol) of 2-fluorobenzyl bromide and 14.21 g (43.62 mmol) of cesium carbonate were then added. The mixture was stirred at RT for two hours. The reaction mixture was then poured onto water (1.17 l) and extracted twice with ethyl acetate (502 ml). The collected organic phases were washed with saturated aqueous sodium chloride solution (335 ml), dried, filtered and concentrated. The residue was chromatographed on silica gel (eluent: 97:3 petroleum ether/ethyl acetate) and the product fractions were concentrated. This gave 9.0 g (61% of theory) of the desired compound in solid form. The solid was taken up in ethyl acetate and washed with 10% aqueous sodium thiosulfate solution and then with saturated aqueous sodium chloride solution, dried and concentrated.

LC-MS (method 2): $R_t$=2.57 min

MS (ESIpos): m/z=372 (M+H)$^+$ $^1$H NMR (400 MHz, DMSO-d$_6$): δ=5.73 (s, 2H), 7.13-7.26 (m, 3H), 7.33-7.41 (m, 1H), 7.94 (dd, 1H), 8.69-8.73 (m, 1H).

Example 8A 5-fluoro-1-(2-fluorobenzyl)-1H-pyrazolo[3,4-b]pyridine-3-carbonitrile

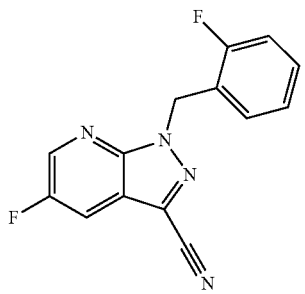 [SMILES: N#Cc1nn(Cc2ccccc2F)c2ncc(F)cc12]

A suspension of 16.03 g (43.19 mmol) of 5-fluoro-1-(2-fluorobenzyl)-3-iodo-1H-pyrazolo[3,4-b]pyridine (Example 7A) and 4.25 g (47.51 mmol) of copper cyanide was initially charged in DMSO (120 ml) and stirred at 150° C. for 2 h. After cooling, the contents of the flask were cooled to about 40° C. and poured onto a solution of conc. aqueous ammonia (90 ml) and water (500 ml), ethyl acetate (200 ml) was added and the mixture was stirred briefly. The aqueous phase was removed and extracted twice more with ethyl acetate (200 ml each time). The combined organic phases were washed twice with 10% aqueous sodium chloride solution (100 ml each time), dried over sodium sulfate and concentrated under reduced pressure. The crude product was converted without further purification.

Yield: 11.1 g (91% of theory)

$^1$H NMR (400 MHz, DMSO-d$_6$): δ=5.87 (s, 2H), 7.17-7.42 (m, 4H), 8.52 (dd, 1H), 8.87 (dd, 1H).

Example 9A 5-fluoro-1-(2-fluorobenzyl)-1H-pyrazolo[3,4-b]pyridine-3-carboximidamide acetate

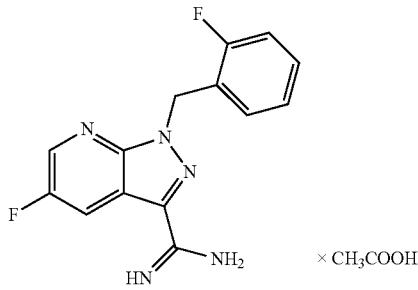 [SMILES: N=C(N)c1nn(Cc2ccccc2F)c2ncc(F)cc12]

11.1 g (41.07 mmol) of 5-fluoro-1-(2-fluorobenzyl)-1H-pyrazolo[3,4-b]pyridine-3-carbonitrile (Example 8A) were added to 2.22 g (41.07 mmol) of sodium methoxide in methanol (270 ml), and the mixture was stirred at RT for 2 h. 2.64 g (49.29 mmol) of ammonium chloride and acetic acid (9.17 ml) were then added, and the mixture was heated to reflux overnight. It was then concentrated to dryness and the residue was taken up in water (100 ml) and ethyl acetate (100 ml) and adjusted to a pH of 10 using 2N aqueous sodium hydroxide solution. The mixture was stirred vigorously at RT for about 1 h. The resulting suspension was filtered with suction and washed through with ethyl acetate (100 ml), with water (100 ml) and once more with ethyl acetate (100 ml). The residue was dried under high vacuum over phosphorus pentoxide.

Yield: 9.6 g (78% of theory)

MS (ESIpos): m/z=288 (M+H)$^+$ $^1$H NMR (400 MHz, DMSO-d$_6$): δ=1.85 (s, 3H), 5.80 (s, 2H), 7.14-7.25 (m, 3H), 7.36 (m, 1H), 8.42 (dd, 1H), 8.72 (dd, 1H).

Example 10A methyl 3,3-dicyano-2,2-dimethylpropanoate

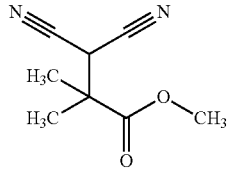

In THF (91 ml), 1.816 g (45.411 mmol) of sodium hydride (60% in mineral oil) were admixed gradually with 3 g (45.411 mmol) of malononitrile. Subsequently, 5.876 ml (45.411 mmol) of methyl 2-bromo-2-methylpropanoate were added and the mixture was stirred at room temperature overnight. Thereafter, another 5.876 ml (45.411 mmol) of methyl 2-bromo-2-methylpropanoate were added and the mixture was heated to 50° C. overnight. Then yet another 1.762 ml (13.623 mmol) of methyl 2-bromo-2-methylpropanoate were added and the mixture was heated to 50° C. for a further 4 h. The mixture was then admixed with saturated aqueous sodium hydrogencarbonate solution and extracted three times with ethyl acetate. The combined organic phases were washed with saturated aqueous sodium chloride solution, dried over sodium sulfate, filtered and concentrated to dryness. This gave 8.9 g of crude product, which was purified by chromatography on silica gel (4:1 cyclohexane-ethyl acetate).

Yield: 6.47 g (85% of theory)

$^1$H NMR (400 MHz, DMSO-d$_6$): δ [ppm]=1.40 (s, 6H), 3.74 (s, 3H), 5.27 (s, 1H).

Example 11A methyl 3-bromotetrahydrofuran-3-carboxylate

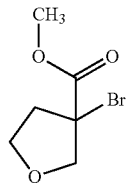

5.0 g (38.419 mmol) of methyl tetrahydrofuran-3-carboxylate (prepared analogously to: *J. Org. Chem.* 1996, 2690) were dissolved in 200 ml of THF and cooled to −78° C., and then 76.83 ml of a 1M solution of lithium bis(trimethylsilyl) amide in THF were added. After 30 min at −78° C., 10.26 g (57.63 mmol) of N-bromosuccinimide suspended in 50 ml of THF were added gradually. Thereafter, the mixture was left to warm up to RT overnight. The mixture was then admixed with water and extracted with ethyl acetate. The phases were separated and the aqueous phase was extracted twice more with ethyl acetate. The combined organic phases were washed with saturated aqueous sodium chloride solution and then dried over sodium sulfate, filtered and concentrated. The crude product was purified by means of chromatography on silica gel (eluent: dichloromethane). This gave 491 mg (6% of theory) of the target compound.

$^1$H NMR (400 MHz, CDCl$_3$): δ [ppm]=2.49 (ddd, 1H), 2.74 (ddd, 1H), 3.83 (s, 3H), 4.03-4.10 (m, 1H), 4.11-4.17 (m, 2H), 4.31 (d, 1H).

Example 12A methyl 3-(dicyanomethyl)tetrahydrofuran-3-carboxylate

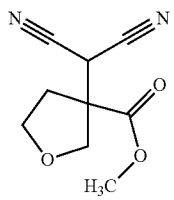

440 mg (11.00 mmol) of sodium hydride (60% in mineral oil) were initially charged in 30 ml of THF, and 726 mg (11.00 mmol) of malononitrile were added in portions. Thereafter, 2.3 g (11.00 mmol) of the compound obtained in example 11A in THF (50 ml) were added. The mixture was stirred at RT for 6 h and then heated to 50° C. overnight. After cooling, the mixture was admixed with saturated aqueous sodium hydrogencarbonate solution and extracted three times with ethyl acetate. The combined organic phases were washed with saturated aqueous sodium chloride solution and then dried over sodium sulfate, filtered and concentrated. The residue (2.66 g) was dried under high vacuum for 1 h and then converted without further purification.

Example 13A 2-methoxy-4-methyl-6-oxo-1,4,5,6-tetrahydropyridine-3-carbonitrile

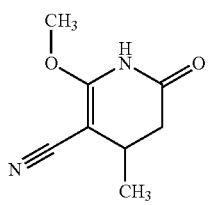

The synthesis of the compound is described: *Heterocycles,* 1985; 1135-1141.

Example 14A 2-methoxy-6-oxo-4-(trifluoromethyl)-1,4,5,6-tetrahydropyridine-3-carbonitrile

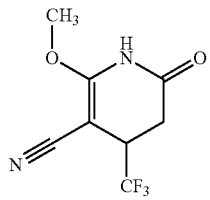

7.47 g (138.39 mmol) of sodium methoxide in methanol (85 ml) were initially charged with ice cooling, and 6.04 g (91.44 mmol) of malononitrile were added in portions. Subsequently, 11.84 g (76.84 mmol) of methyl 4,4,4-trifluorocrotonate were added dropwise while stirring, and the mixture was stirred at room temperature for 30 min and then heated to reflux for 1 h. Thereafter, the mixture was concentrated to dryness under reduced pressure. The residue was admixed with water and extracted four times with ethyl acetate. The combined organic phases were dried over sodium sulfate, filtered and concentrated. Further purification was effected by chromatography on silica gel (3:1 cyclohexane-ethyl acetate). This gave 1.95 g of the target compound (11% of theory).

LC-MS (method 1): R$_t$=0.61 min; MS (ESIpos): m/z=221 (M+H)$^+$

Example 15A 5-fluoro-3-iodo-1H-pyrazolo[3,4-b]pyridine

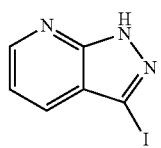

The synthesis is described in in WO 2006/130673, Scheme D.

Example 16A 3-iodo-1-(3,3,4,4,4-pentafluorobutyl)-1H-pyrazolo[3,4-b]pyridine

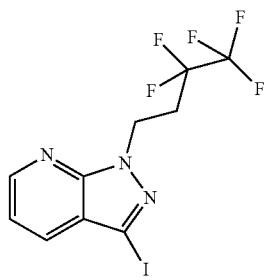 [SMILES: FC(F)(F)C(F)(F)CCn1nc(I)c2cccnc21]

10.00 g (40.813 mmol) of Example 15A were initially charged in DMF (170 ml), and then 12.30 g (44.894 mmol) of 1,1,1,2,2-pentafluoro-4-iodobutane in DMF (30 ml) and 14.628 g (44.894 mmol) of cesium carbonate were added. The mixture was stirred at RT for 2 days. Subsequently, another 12.30 g (44.894 mmol) of 1,1,1,2,2-pentafluoro-4-iodobutane and 14.628 g (44.894 mmol) of cesium carbonate were added and the mixture was stirred at RT for 2 days. Thereafter, 3.485 g (12.720 mmol) of 1,1,1,2,2-pentafluoro-4-iodobutane and 4.145 g (12.720 mmol) of cesium carbonate were added and the mixture was stirred at RT overnight. After this period, 5.00 g (18.250 mmol) of 1,1,1,2,2-pentafluoro-4-iodobutane and 5.946 g (18.250 mmol) of cesium carbonate were added and the mixture was stirred at room temperature for 6 days. The mixture was then stirred at 70° C. for 2 days. Solids were filtered off with suction and washed with DMF, and then the liquid was concentrated under high vacuum. The residue was purified by preparative HPLC (methanol:water (with 0.1% formic acid) gradient). This gave 5.48 g (34% of theory) of the title compound in solid form.

LC-MS (method 3): $R_t$=1.23 min

MS (ESIpos): m/z=392 (M+H)$^+$

1H NMR (400 MHz, DMSO-d6): δ=2.87-3.00 (m, 2H), 4.81 (t, 2H), 7.33 (dd, 1H), 7.97 (dd, 1H), 8.65 (dd, 1H).

Example 17A 1-(3,3,4,4,4-pentafluorobutyl)-1H-pyrazolo[3,4-b]pyridine-3-carbonitrile

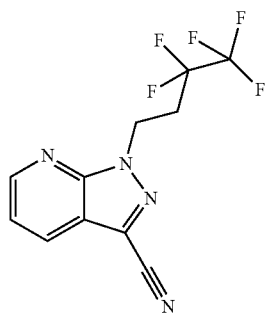 [SMILES: N#Cc1nn(CCC(F)(F)C(F)(F)F)c2ncccc12]

A suspension of 5.480 g (14.012 mmol) of example 16A and 1.380 g (15.414 mmol) of copper(I) cyanide was initially charged in DMSO (50 ml) and stirred at 150° C. for 3 h. After cooling, the mixture was filtered through Celite and washed through with ethyl acetate and THF. This was followed by washing four times with a solution of sat. aq. ammonium chloride solution and conc. aqueous ammonia (3:1, v/v) and then with sat. aq. sodium chloride solution. The organic phase was dried over sodium sulfate, filtered and concentrated, and then dried under high vacuum.

Yield: 3.59 g (88% of theory)

LC-MS (method 1): $R_t$=1.04 min

MS (ESIpos): m/z=291 (M+H)$^+$

1H NMR (400 MHz, DMSO-d6): δ=2.97-3.10 (m, 2H), 4.94 (t, 2H), 7.55 (dd, 1H), 8.51 (dd, 1H), 8.81 (dd, 1H).

Example 18A 1-(3,3,4,4,4-pentafluorobutyl)-1H-pyrazolo[3,4-b]pyridine-3-carboximidamide acetate

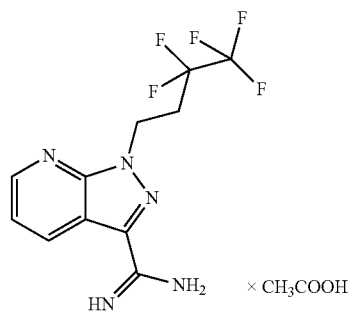 [SMILES: N=C(N)c1nn(CCC(F)(F)C(F)(F)F)c2ncccc12]

3.59 g (12.371 mmol) of Example 17A in methanol (20 ml) were added to 0.668 g (12.371 mmol) of sodium methoxide in methanol (40 ml), and the mixture was stirred at RT for 2 h. 0.794 g (14.845 mmol) of ammonium chloride and acetic acid (2.762 ml) were then added, and the mixture was heated to reflux overnight. Thereafter, the mixture was concentrated to dryness and the residue was admixed with ethyl acetate and 1N sodium hydroxide solution. The mixture was stirred vigorously at RT for about 1 h. The resulting solids were filtered off with suction and washed with ethyl acetate and water. The residue under high vacuum dried. This gave 0.507 g (11% of theory, 100% purity). In the case of the wash fractions, the phases were separated and the aqueous phase was extracted twice with ethyl acetate. The combined organic phases were washed with water and sat. aq. sodium chloride solution, dried over sodium sulfate, filtered and concentrated, and then dried under high vacuum. This gave a further 2.76 g (43% of theory, 71% purity).

LC-MS (method 1): $R_t$=0.58 min

MS (ESIpos): m/z=308 (M+H)$^+$ $^1$H NMR (400 MHz, DMSO-d$_6$): δ=1.84 (s, 3H), 2.95-3.08 (m, 2H), 4.85 (t, 2H), 7.39 (dd, 1H), 8.63-8.67 (m, 2H).

Example 19A 5-fluoro-3-iodo-1-(3,3,4,4,4-pentafluorobutyl)-1H-pyrazolo[3,4-b]pyridine

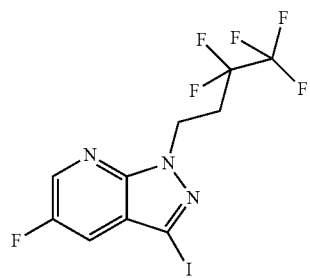 [SMILES: Fc1cnc2c(c1)c(I)nn2CCC(F)(F)C(F)(F)F]

5.0 g (19.010 mmol) of 5-fluoro-3-iodo-1H-pyrazolo[3,4-b]pyridine were initially charged in DMF (100 ml), and then 20.83 g (76.042 mmol) of 1,1,1,2,2-pentafluoro-4-iodobutane, and also 14.86 g (45.65 mmol) of cesium carbonate and 0.63 g (3.802 mmol) of potassium iodide were added. The mixture was stirred at 140° C. overnight. The mixture was then cooled and combined with a prior experiment which proceeded analogously from 200 mg of 5-fluoro-3-iodo-1H-pyrazolo[3,4-b]pyridine. Solids were filtered off with suction and washed with DMF, and then the liquid was concentrated under high vacuum. The residue was purified by means of preparative HPLC (methanol:water gradient). This gave 4.34 g (52% of theory) of the title compound in solid form.

LC-MS (method 3): $R_t$=1.30 min
MS (ESIpos): m/z=410 (M+H)$^+$
$^1$H NMR (400 MHz, DMSO-d$_6$): δ=2.84-3.00 (m, 2H), 4.79 (t, 2H), 7.93 (dd, 1H), 8.71 (dd, 1H).

Example 20A 5-fluoro-1-(3,3,4,4,4-pentafluorobutyl)-1H-pyrazolo[3,4-b]pyridine-3-carbonitrile

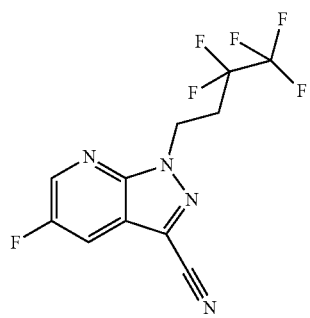 [SMILES: N#Cc1nn(CCC(F)(F)C(F)(F)F)c2ncc(F)cc12]

A suspension of 4.34 g (10.609 mmol) of Example 19A and 1.045 g (11.670 mmol) of copper(I) cyanide was initially charged in DMSO (30 ml) and stirred at 150° C. for 2 h. After cooling, the mixture was filtered through Celite, washed through with ethyl acetate and THF and then extracted four times with a solution of sat. aqueous ammonium chloride solution and conc. aqueous ammonia (3:1 v/v). The combined organic phases were washed with saturated aqueous sodium chloride solution, dried over sodium sulfate, filtered and concentrated under reduced pressure.

Yield: 3.19 g (97% of theory)
1H NMR (400 MHz, DMSO-d6): δ=2.94-3.09 (m, 2H), 4.93 (t, 2H), 8.54 (dd, 1H), 8.88 (dd, 1H).

Example 21A 5-fluoro-1-(3,3,4,4,4-pentafluorobutyl)-1H-pyrazolo[3,4-b]pyridine-3-carboximidamide acetate

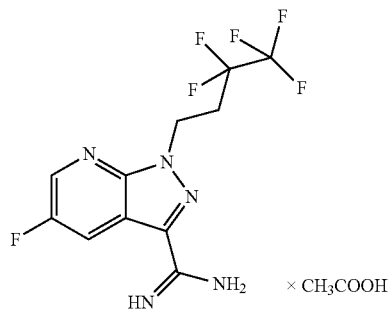 [SMILES: N=C(N)c1nn(CCC(F)(F)C(F)(F)F)c2ncc(F)cc12]

3.19 g (10.351 mmol) of Example 20A were added to 0.559 g (10.351 mmol) of sodium methoxide in methanol (25 ml), and the mixture was stirred at RT for 2 h. Thereafter, 0.664 g (12.421 mmol) of ammonium chloride and acetic acid (2.31 ml) were added and the mixture was heated to reflux overnight. Thereafter, the mixture was concentrated to dryness and the residue was admixed with ethyl acetate and 1N sodium hydroxide solution. The phases were separated. The aqueous phase was extracted once again with ethyl acetate. The combined organic phases were combined and concentrated.

Yield: 2.67 g (37% of theory, approx. 56% purity)
LC-MS (method 1): $R_t$=0.68 min
MS (ESIpos): m/z=326 (M+H)±

Working Examples

Example 1

4-amino-2-[1-(2-fluorobenzyl)-1H-pyrazolo[3,4-b]pyridin-3-yl]-5,7-dihydro-6H-pyrrolo[2,3-d]pyrimidin-6-one

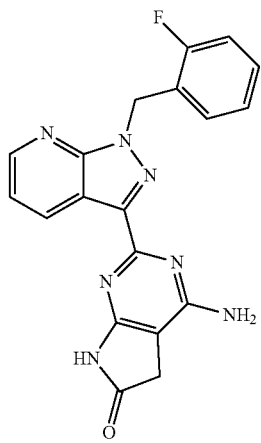 [SMILES: Nc1nc(-c2nn(Cc3ccccc3F)c3ncccc23)nc2c1CC(=O)N2]

Stage a)
1.51 g (37.84 mmol) of sodium hydride (60% in mineral oil) were initially charged in 10 ml of DMSO. Thereafter, while cooling, 2.5 g (37.843 mmol) of malononitrile in DMSO (10 ml) were gradually added dropwise and the mixture was stirred for 10 min. Subsequently, at room temperature, 3.582 ml (37.843 mmol) of methyl bromoacetate in DMSO (10 ml) were added dropwise. The mixture was stirred at RT for a further 2 h. Then the reaction was stopped by addition of saturated aqueous ammonium chloride solution, and ethyl acetate was added. The phases were separated and the aqueous phase was extracted once more with ethyl acetate. The combined organic phases were washed once more with saturated aqueous ammonium chloride solution. This was followed by drying over sodium sulfate, filtration and concentration to dryness. The crude product was used without further purification in step b):

Stage b)
1.04 g (3.403 mmol) of Example 1A were initially charged in tert-butanol, and 458 mg (4.083 mmol) of potassium tert-butoxide were added. Subsequently, 470 mg (3.403 mmol) of the crude product from stage a) in tert-butanol were added and the mixture was heated to reflux overnight. After cooling, water and ethyl acetate were added, and the phases were separated. The aqueous phase was extracted twice with ethyl acetate. The combined organic phases were washed once with water and once with saturated aqueous sodium chloride solution. This was followed by drying over sodium sulfate, filtration and concentration to dryness. The residue was purified by means of preparative HPLC (acetonitrile:water (+0.05% formic acid) gradient). After the product fractions had been concentrated, DMF, water and acetonitrile were added, forming an insoluble residue which was filtered off. After washing the solids with acetonitrile, 23 mg of the target compound were obtained (2% of theory).

LC-MS (method 1): $R_t$=0.82 min; MS (ESIpos): m/z=376 (M+H)$^+$ $^1$H NMR (400 MHz, DMSO-d$_6$): δ [ppm]=3.34 (s, 2H), 5.81 (s, 2H), 6.85 (s br, 2H), 7.13-7.25 (m, 3H), 7.33-7.40 (m, 2H), 8.63 (dd, 1H), 8.99 (dd, 1H), 10.95 (s br, 1H).

Example 2

4-amino-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

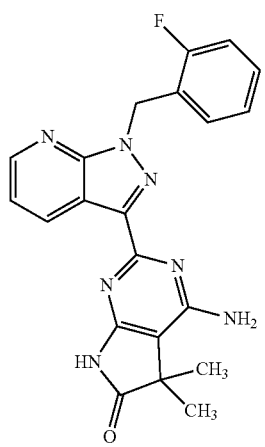 [SMILES: CC1(C)C(=O)Nc2nc(-c3nn(Cc4ccccc4F)c4ncccc34)nc(N)c21]

5.887 g (19.256 mmol) of Example 1A were initially charged in tert-butanol (50 ml), and 2.593 g (23.107 mmol) of potassium tert-butoxide were added. Subsequently, 3.2 g (19.256 mmol) of Example 10A in tert-butanol (25 ml) were added dropwise and the mixture was heated to reflux overnight. The next day, another 0.64 g (3.851 mmol) of Example 10A was added and the mixture was heated to reflux for a further day. After cooling, a precipitate was filtered off, which was washed with diethyl ether. Subsequently, the precipitate was slurried in water, filtered off once more and washed with diethyl ether. After drying under high vacuum, 6.65 g of the target compound were obtained (85% of theory).

LC-MS (method 1): $R_t$=0.90 min; MS (ESIpos): m/z=404 (M+H)±

$^1$H NMR (400 MHz, DMSO-d$_6$): δ [ppm]=1.35 (s, 6H), 5.82 (s, 2H), 6.82 (br s, 2H), 7.14-7.25 (m, 3H), 7.33-7.40 (m, 2H), 8.63 (dd, 1H), 9.03 (dd, 1H), 10.98 (s br, 1H).

Example 3

4-amino-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

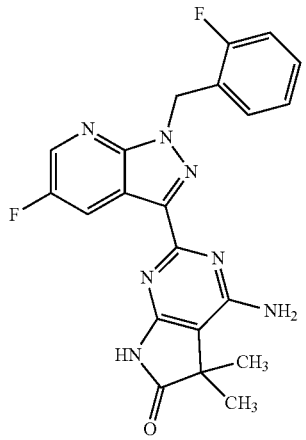 [SMILES: CC1(C)C(=O)Nc2nc(-c3nn(Cc4ccccc4F)c4ncc(F)cc34)nc(N)c21]

In analogy to the preparation of Example 2, 4.18 g (12.035 mmol) of Example 9A were reacted with 2.20 g (13.239 mmol) of Example 10A. 3.72 g of the target compound were obtained (73% of theory).

LC-MS (method 1): $R_t$=0.98 min; MS (ESIpos): m/z=422 (M+H)$^+$ $^1$H NMR (400 MHz, DMSO-d$_6$): δ [ppm]=1.34 (s, 6H), 5.81 (s, 2H), 6.85 (br s, 2H), 7.13-7.25 (m, 3H), 7.36 (m, 1H), 8.69 (dd, 1H), 8.84 (dd, 1H), 10.96 (s br, 1H).

Example 4

4'-amino-2'-[1-(2-fluorobenzyl)-1H-pyrazolo[3,4-b]pyridin-3-yl]-4,5-dihydrospiro[furan-3,5'-pyrrolo[2,3-d]pyrimidine]-6'(7'H)-one

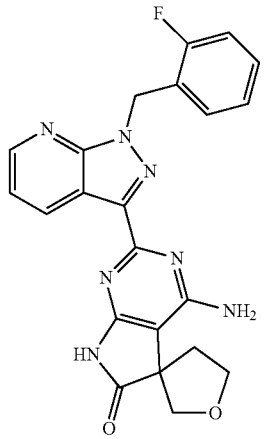 [SMILES: Nc1nc(-c2nn(Cc3ccccc3F)c3ncccc23)nc2c1C1(CCOC1)C(=O)N2]

In analogy to the preparation of Example 2, 2.257 g (7.382 mmol) of Example 1A were reacted with 1.434 g (7.382 mmol) of Example 12A. 566 mg of the target compound were obtained (17% of theory).

LC-MS (method 1): $R_t$=0.84 min; MS (ESIpos): m/z=432 (M+H)$^+$ $^1$H NMR (400 MHz, DMSO-d$_6$): δ [ppm]=2.20-2.37 (m, 2H), 3.71 (d, 1H), 3.90 (q, 1H), 4.10 (d, 1H), 4.25-4.31 (m, 1H), 5.82 (s, 2H), 6.57 (br s, 2H), 7.12-7.25 (m, 3H), 7.33-7.41 (m, 2H), 8.64 (dd, 1H), 9.02 (dd, 1H), 11.96 (s br, 1H).

Example 5

4-amino-2-[1-(2-fluorobenzyl)-1H-pyrazolo[3,4-b]pyridin-3-yl]-5-methyl-5,8-dihydropyrido[2,3-d]pyrimidin-7(6H)-one

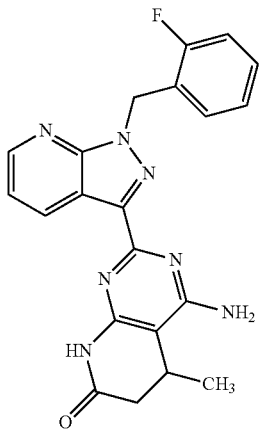 [SMILES: CC1CC(=O)Nc2nc(-c3nn(Cc4ccccc4F)c4ncccc34)nc(N)c21]

2.174 g (7.112 mmol) of Example 1A and 1.3 g (7.823 mmol) of Example 13A were initially charged in 20 ml of methanol, and then 422 mg (7.823 mmol) of sodium methoxide were added in portions at room temperature. The mixture was stirred at room temperature for 10 min and then heated to reflux overnight. After cooling, acetic acid (0.5 ml) and water (20 ml) were added to the mixture and it was cooled in an ice bath. The precipitate was filtered off with suction, washed with water and methanol, and then dried under high vacuum. 2.51 g of the target compound were obtained (87% of theory).

LC-MS (method 1): $R_t$=0.85 min; MS (ESIpos): m/z=404 $(M+H)^+$ $^1$H NMR (400 MHz, DMSO-$d_6$): δ [ppm]=1.04 (d, 3H), 2.31 (d, 1H), 2.79 (dd, 1H), 3.13-3.19 (m, 1H), 5.81 (s, 2H), 6.93 (br s, 2H), 7.12-7.25 (m, 3H), 7.34-7.37 (m, 2H), 8.62 (dd, 1H), 9.14 (dd, 1H), 10.56 (s, 1H).

Example 6

4-amino-2-[1-(2-fluorobenzyl)-1H-pyrazolo[3,4-b]pyridin-3-yl]-5-(trifluoromethyl)-5,8-dihydropyrido[2,3-d]pyrimidin-7(6H)-one

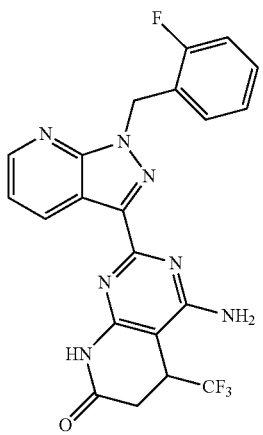 [SMILES: Nc1nc(-c2nn(Cc3ccccc3F)c3ncccc23)nc2c1C(C(F)(F)F)CC(=O)N2]

694 mg (2.271 mmol) of Example 1A and 500 mg (2.271 mmol) of Example 14A were initially charged in 10 ml of t-butanol, and then 305 mg (2.725 mmol) of potassium tert-butoxide were added in portions at room temperature. The mixture was stirred at room temperature for 10 min and then heated to reflux for 2 days. After cooling, water and ethyl acetate were added to the mixture. The precipitate was filtered off with suction. The filtrate was concentrated, a little ethyl acetate and diethyl ether were added, and the precipitate formed was filtered off with suction. The combined solids from the two component steps were subsequently dried under high vacuum. 588 mg of the target compound were obtained (53% of theory).

LC-MS (method 1): Rt=0.92 min; MS (ESIpos): m/z=458 $(M+H)^+$ $^1$H NMR (400 MHz, DMSO-d6): δ [ppm]=2.63 (d, 1H), 3.19 (dd, 1H), 4.16-4.20 (m, 1H), 5.83 (s, 2H), 7.13-7.40 (m, 7H), 8.63 (dd, 1H), 9.15 (dd, 1H), 10.85 (s, 1H).

Example 7

4-amino-5,5-dimethyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one

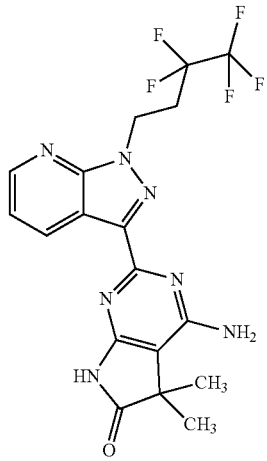 [SMILES: CC1(C)C(=O)Nc2nc(-c3nn(CCC(F)(F)C(F)(F)F)c4ncccc34)nc(N)c21]

500 mg (1.361 mmol) of Example 18A were initially charged in tert-butanol (7.5 ml), and 183 mg (1.361 mmol) of potassium tert-butoxide were added. Subsequently, 226 mg (1.361 mmol) of Example 10A in tert-butanol (2.5 ml) were added dropwise and the mixture was heated to reflux overnight. After cooling, ethyl acetate and water were added, the phases were separated and the aqueous phase was extracted twice with ethyl acetate. The combined organic phases were washed with sat. aq. sodium chloride solution, dried over sodium sulfate, filtered and concentrated. The residue was stirred with methanol and a solid was filtered off with suction. This solid was washed vigorously with methanol, and the combined filtrates were concentrated and then purified by means of preparative HPLC (acetonitrile:water (+0.05% formic acid) gradient). 127 mg of the title compound were obtained (21% of theory).

LC-MS (method 1): $R_t$=0.93 min; MS (ESIpos): m/z=442 $(M+H)^{+1}$H NMR (400 MHz, DMSO-$d_6$): δ [ppm]=1.36 (s, 6H), 2.91-3.04 (m, 2H), 4.88 (t, 2H), 6.83 (br s, 2H), 7.38 (dd, 1H), 8.63 (dd, 1H), 9.02 (dd, 1H), 11.01 (s br, 1H).

Example 8

4-amino-2-[5-fluoro-1-(3,3,4,4,4-pentafluorobutyl)-1H-pyrazolo[3,4-b]pyridin-3-yl]-5,5-dimethyl-5,7-dihydro-6H-pyrrolo[2,3-d]pyrimidin-6-one

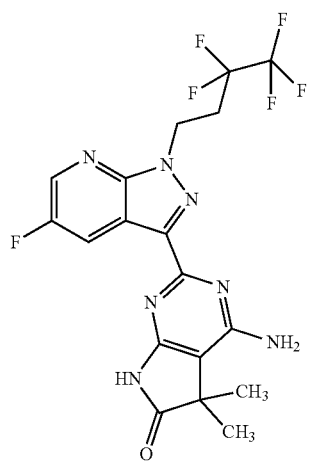 [SMILES: CC1(C)C(=O)Nc2nc(-c3nn(CCC(F)(F)C(F)(F)F)c4ncc(F)cc34)nc(N)c21]

520 mg (1.350 mmol) of Example 21A were initially charged in tert-butanol (10 ml), and 181 mg (1.620 mmol) of potassium tert-butoxide were added. Subsequently, 224 mg (1.350 mmol) of Example 10A in tert-butanol (2.5 ml) were added and the mixture was heated to reflux overnight. Subsequently, another 112 mg (0.675 mmol) of Example 10A were added and the mixture was heated to reflux for a further 7.5 h. After cooling, water and ethanol were added and the mixture was treated in an ultrasound bath for 1 h. This formed a precipitate, which was filtered off with suction and washed with water. The filtercake was stirred with a little ethanol (2-3 ml) and filtered with suction once again. The solids were dried under high vacuum. 212 mg of the title compound were obtained (34% of theory).

LC-MS (method 1): $R_t$=1.01 min; MS (ESIpos): m/z=460 $(M+H)^+$ $^1$H NMR (400 MHz, DMSO-$d_6$): δ [ppm]=1.36 (s, 6H), 2.92-3.04 (m, 2H), 4.87 (t, 2H), 6.88 (br s, 2H), 8.71 (s br, 1H), 8.85 (dd, 1H), 11.01 (s br, 1H).

B. ASSESSMENT OF PHARMACOLOGICAL EFFICACY

The pharmacological action of the inventive compounds can be shown in the following assays:

B-1. Vasorelaxant Action In Vitro

Rabbits are stunned by a blow to the neck and exsanguinated. The aorta is removed, freed from adhering tissue and divided into rings of width 1.5 mm, which are placed individually under prestress into 5 ml organ baths with carbogen-sparged Krebs-Henseleit solution at 37° C. having the following composition (each mM): sodium chloride 119; potassium chloride: 4.8; calcium chloride dihydrate: 1; magnesium sulfate heptahydrate: 1.4; potassium dihydrogenphosphate: 1.2; sodium hydrogencarbonate: 25; glucose: 10. The contractile force is determined with Statham UC2 cells, amplified and digitalized using A/D transducers (DAS-1802 HC, Keithley Instruments Munich), and recorded in parallel on linear recorders. To obtain a contraction, phenylephrine is added to the bath cumulatively in increasing concentration. After several control cycles, the substance to be studied is added in increasing dosage each time in every further run, and the magnitude of the contraction is compared with the magnitude of the contraction attained in the last preceding run. This is used to calculate the concentration needed to reduce the magnitude of the control value by 50% ($IC_{50}$ value). The standard administration volume is 5 nl; the DMSO content in the bath solution corresponds to 0.1%.

Representative $IC_{50}$ values for the inventive compounds are shown in the table below (table 1):

TABLE 1

| Example No. | $IC_{50}$ [nM] |
|---|---|
| 2 | 48 |
| 3 | 9.3 |
| 4 | 24 |

B-2. Effect on a Recombinant Guanylate Cyclase Reporter Cell Line

The cellular action of the inventive compounds is determined on a recombinant guanylate cyclase reporter cell line as described in F. Wunder et al., *Anal. Biochem.* 339, 104-112 (2005).

Representative values (MEC=minimal effective concentration) for the inventive compounds are shown in the table below (table 2):

TABLE 2

| Example No. | MEC [μM] |
|---|---|
| 2 | 0.001 |
| 3 | 0.001 |
| 4 | 0.003 |

B-3. Radiotelemetric Measurement of Blood Pressure on Conscious, Spontaneously Hypertensive Rats A commercially available telemetry system from DATA SCIENCES INTERNATIONAL DSI, USA, is used for the blood pressure measurement on conscious rats described below.

The system consists of 3 main components:
implantable transmitters (Physiotel® telemetry transmitter)
receivers (Physiotel® receivers) which are connected via a multiplexer (DSI Data Exchange Matrix) to a
data acquisition computer.

The telemetry system makes it possible to continuously record blood pressure, heart rate and body motion of conscious animals in their usual habitat.

Animal Material

The investigations are carried out on adult female spontaneously hypertensive rats (SHR Okamoto) with a body weight of >200 g. SHR/NCrl from the Okamoto Kyoto School of Medicine, 1963, were a cross of male Wistar Kyoto rats with greatly elevated blood pressure and female rats having slightly elevated blood pressure, and were handed over at F13 to the U.S. National Institutes of Health.

After transmitter implantation, the experimental animals are housed individually in type 3 Makrolon cages. They have free access to standard feed and water.

The day/night rhythm in the experimental laboratory is changed by the room lighting at 6:00 am and at 7:00 pm.

Transmitter Implantation

The TA11 PA—C40 telemetry transmitters used are surgically implanted under aseptic conditions in the experimental animals at least 14 days before the first experimental use. The animals instrumented in this way can be used repeatedly after the wound has healed and the implant has settled.

For the implantation, the fasted animals are anesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and wound is closed layer by layer.

An antibiotic (Tardomyocel COMP, Bayer, 1 ml/kg s.c.) is administered postoperatively for prophylaxis of infection.

Substances and Solutions

Unless stated otherwise, the substances to be studied are administered orally by gavage to a group of animals in each case (n=6). In accordance with an administration volume of 5 ml/kg of body weight, the test substances are dissolved in suitable solvent mixtures or suspended in 0.5% Tylose.

A solvent-treated group of animals is used as a control.

Test Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch. They are switched to transmission in the run-up to the experiment. The signals emitted can be recorded online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measured values is repeated under computer control at 5-minute intervals. The source data obtained as absolute values are corrected in the diagram with the currently measured barometric pressure (Ambient Pressure Reference Monitor; APR-1) and stored as individual data. Further technical details are given in the extensive documentation from the manufacturer company (DSI).

Unless stated otherwise, the test substances are administered at 9.00 am on the day of the experiment. Following the administration, the parameters described above are measured over 24 hours.

Evaluation

After the end of the experiment, the acquired individual data are sorted using the analysis software (DATAQUEST™ A.R.T.™ ANALYSIS). The blank value is assumed to be the time 2 hours before administration, and so the selected data set encompasses the period from 7.00 am on the day of the experiment to 9.00 am the following day.

The data are smoothed over an adjustable period by determination of the average (15-minute average) and transferred as a text file to a storage medium. The measured values presorted and compressed in this way are transferred to Excel templates and tabulated. For each day of the experiment, the data obtained are stored in a dedicated file bearing the experiment number. Results and test protocols are filed in paper form sorted by numbers.

Literature

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994

C. WORKING EXAMPLES FOR PHARMACEUTICAL COMPOSITIONS

The inventive compounds can be converted to pharmaceutical formulations as follows.

Tablet:

Composition:

100 mg of the inventive compound, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.

Production:

The mixture of inventive compound, lactose and starch is granulated with a 5% solution (w/w) of the PVP in water. The granules are dried and mixed with the magnesium stearate for 5 minutes. This mixture is pressed with a conventional tableting press (for tablet format see above). The guide value used for the pressing is a pressing force of 15 kN.

Suspension for Oral Administration:

Composition:

1000 mg of the inventive compound, 1000 mg of ethanol (96%), 400 mg of Rhodigel® xanthan gum from FMC, Pennsylvania, USA) and 99 g of water.

A single dose of 100 mg of the inventive compound corresponds to 10 ml of oral suspension.

Production:

The Rhodigel is suspended in ethanol; the inventive compound is added to the suspension. The water is added while stirring. The mixture is stirred for about 6 h until the swelling of the Rhodigel is complete.

Solution for Oral Administration:

Composition:

500 mg of the inventive compound, 2.5 g of polysorbate and 97 g of polyethylene glycol 400. A single dose of 100 mg of the inventive compound corresponds to 20 g of oral solution.

Production:

The inventive compound is suspended in the mixture of polyethylene glycol and polysorbate while stirring. The stirring operation is continued until dissolution of the inventive compound is complete.

i.v. Solution:

The inventive compound is dissolved in a concentration below the saturation solubility in a physiologically acceptable solvent (e.g. isotonic saline, 5% glucose solution and/or 30% PEG 400 solution). The solution is subjected to sterile filtration and dispensed into sterile and pyrogen-free injection vessels.

The invention claimed is:
1. A compound of the formula (I)

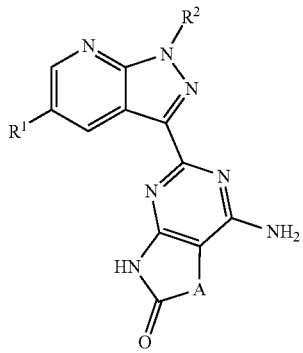

in which
A is $(C_1-C_3)$-alkanediyl or a group of the formula

where
* is the attachment site to the pyrimidine ring,
# is the attachment site to the carbonyl group,
the ring Q is a 4- to 6-membered heterocycle,
and
where $(C_1-C_3)$-alkanediyl may be substituted by 1 or 2 substituents independently selected from the group of fluorine, trifluoromethyl, $(C_1-C_4)$-alkyl, hydroxyl and amino,
in which $(C_1-C_4)$-alkyl may be substituted by 1 to 3 substituents independently selected from the group of fluorine, trifluoromethyl and hydroxyl,
$R^1$ is hydrogen or fluorine,
$R^2$ is $(C_1-C_6)$-alkyl or benzyl,
where $(C_1-C_6)$-alkyl is substituted by one trifluoromethyl substituent,
where $(C_1-C_6)$-alkyl may be substituted by 1 to 3 fluorine substituents,
and
where benzyl is substituted by 1 to 3 fluorine substituents,
or N-oxides, salts, solvates, salts of the N-oxides and solvates of the N-oxides or salts thereof.
2. The compound of claim 1, in which
A is a group of the formula

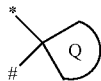

where
* is the attachment site to the pyrimidine ring,
# is the attachment site to the carbonyl group,
the ring Q is an azetidinyl, oxetanyl, pyrrolidinyl, tetrahydrofuranyl, piperidinyl or tetrahydropyranyl ring,
$R^1$ is hydrogen or fluorine,
$R^2$ is 2,2,2-trifluoroethyl, 3,3,3-trifluoroprop-1-yl, 4,4,4-trifluorobut-1-yl, 3,3,4,4,4-pentafluorobut-1-yl or benzyl,
where benzyl is substituted by 1 to 3 fluorine substituents,
or salts, solvates and solvates of the salts thereof.
3. The compound of claim 1, in which
A is $(C_1-C_3)$-alkanediyl
where $(C_1-C_3)$-alkanediyl may be substituted by 1 or 2 substituents independently selected from the group of fluorine, $(C_1-C_4)$-alkyl, hydroxyl and amino,
and
where $(C_1-C_3)$-alkanediyl is substituted by 1 substituent selected from the group of fluorine and trifluoromethyl,
$R^1$ is hydrogen or fluorine,
$R^2$ is 2,2,2-trifluoroethyl, 3,3,3-trifluoroprop-1-yl, 4,4,4-trifluorobut-1-yl, 3,3,4,4,4-pentafluorobut-1-yl or benzyl,
where benzyl is substituted by 1 to 3 fluorine substituents,
or salts, solvates and solvates of the salts thereof.
4. A process for preparing a compound of formula (I) as defined in claim 1, comprising:
[A] converting a compound of the formula (II)

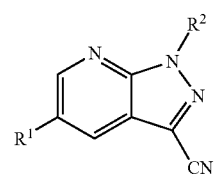

in which $R^1$ and $R^2$ are each as defined in claim 1,
under acidic conditions to a compound of the formula (III)

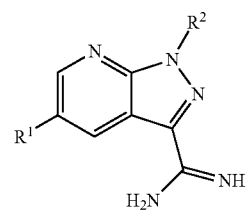

in which $R^1$ and $R^2$ are each as defined in claim 1,
reacting the compound of formula (III) in an inert solvent in the presence of a suitable base with a compound of the formula (IV)

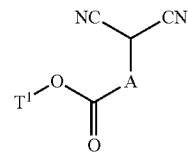

in which A is as defined in claim 1 and
$T^1$ is $(C_1-C_4)$-alkyl, to give a compound of the formula (I)

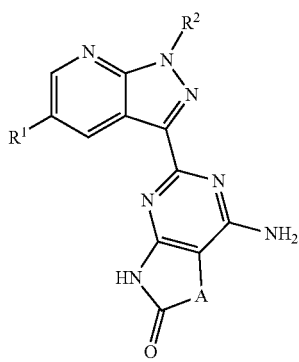

(I)

in which A, R¹ and R² are each as defined in claim 1, or

[B] reacting the compound of the formula (III) in an inert solvent in the presence of a suitable base with a compound of the formula (V)

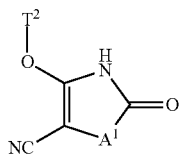

(V)

in which
$A^1$ is $(C_2\text{-}C_3)$-alkanediyl,
where $(C_2\text{-}C_3)$-alkanediyl may be substituted by 1 or 2 substituents independently selected from the group of fluorine, trifluoromethyl and $(C_1\text{-}C_4)$-alkyl, in which $(C_1\text{-}C_4)$-alkyl may be substituted by 1 to 3 substituents independently selected from the group of fluorine, trifluoromethyl and hydroxyl,
and
$T^2$ is $(C_1\text{-}C_4)$-alkyl,
to give a compound of the formula (I-A)

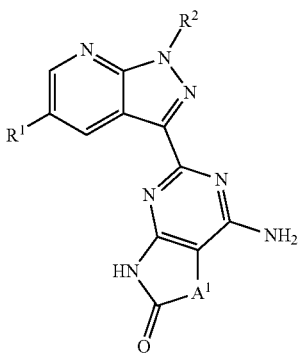

(I-A)

in which $A^1$, $R^1$ and $R^2$ are each as defined in claim 1,
wherein the resulting compound of formula (I) or formula (I-A) is optionally converted with the appropriate (i) solvent and/or (ii) acid or base into a solvate, salt and/or solvate of the salt thereof.

5. A pharmaceutical composition comprising a compound of claim 1 and an inert, nontoxic, pharmaceutically suitable excipient.

6. The pharmaceutical composition of claim 5, further comprising an active ingredient selected from the group consisting of an organic nitrate, an NO donor, a cGMP-PDE inhibitor, an antithrombotic agent, a hypotensive agent and a lipid metabolism modifier.

* * * * *